US011447795B2

(12) United States Patent
Lu et al.

(10) Patent No.: US 11,447,795 B2
(45) Date of Patent: Sep. 20, 2022

(54) PLANTS HAVING ENHANCED TOLERANCE TO INSECT PESTS AND RELATED CONSTRUCTS AND METHODS INVOLVING INSECT TOLERANCE GENES

(71) Applicants: PIONEER OVERSEAS CORPORATION, Johnston, IA (US); SINOBIOWAY BIO-AGRICULTURE GROUP CO LTD., Beijing (CN)

(72) Inventors: Guihua Lu, Beijing (CN); Guanfan Mao, Beijing (CN); Guokui Wang, Beijing (CN); Feng Zhong, Beijing (CN)

(73) Assignee: SINOBIOWAY BIO-AGRICULTURE GROUP CO LTD PIONEER OVERSEAS CORPORATION

( * ) Notice: Subject to any disclaimer, the term of this patent is extended or adjusted under 35 U.S.C. 154(b) by 49 days.

(21) Appl. No.: 16/963,382

(22) PCT Filed: Jan. 23, 2019

(86) PCT No.: PCT/CN2019/072815
§ 371 (c)(1),
(2) Date: Jul. 20, 2020

(87) PCT Pub. No.: WO2019/144882
PCT Pub. Date: Aug. 1, 2019

(65) Prior Publication Data
US 2021/0363539 A1 Nov. 25, 2021

(30) Foreign Application Priority Data
Jan. 24, 2018 (CN) .......................... 201810067456.8

(51) Int. Cl.
*C12N 15/82* (2006.01)
*C07K 14/41* (2006.01)
*C07K 14/415* (2006.01)

(52) U.S. Cl.
CPC ........ *C12N 15/8286* (2013.01); *C07K 14/415* (2013.01)

(58) Field of Classification Search
CPC .......................... C12N 15/8286; A01H 6/4636
See application file for complete search history.

(56) References Cited

U.S. PATENT DOCUMENTS

2004/0123343 A1* 6/2004 La Rosa .............. C07K 14/415
800/278
2007/0020621 A1* 1/2007 Boukharov ........ C12N 15/8227
435/6.12

FOREIGN PATENT DOCUMENTS

WO WO-2013080203 A1 * 6/2013 ......... C12N 15/8243
WO 2015148976 10/2015

OTHER PUBLICATIONS

Du et al (CP018159.1, published May 4, 2017). (Year: 2017).*
Matsumoto et al (Tobacco and Arabidopsis SLT1 mediate salt tolerance of yeast. Plant Molecular Biology 45: 489-500, 2001) (Year : 2001).*
The Rice Chromosome 3 Sequencing Consortium (Sequence, annotation, and analysis of synteny between rice chromosome 3 and diverged grass species. Genome Research. 1284-1291, 2005) (Year: 2006).*
Sakai et al (Rice Annotation Project Database (RAP-DB): An Integrative and Interactive Database for Rice Genomics. Plant Cell Physiol. 54: 1-11, 2013) (Year: 2013).*
International Search Report and Written Opinion PCT/CN2018/113324, dated Apr. 23, 2019.
Predicted: *Oryza sativa Japonica* Group uncharacterized LOC4332419, transcript variant X1, mRNA, Genbank: XM_015775443.1, Mar. 1, 2016.
Predicted: *Oryza sativa Japonica* Group uncharacterized LOC4327202, mRNA, Genbank: XM_015759115.1, Mar. 1, 2016.
Kikuchi et al. *Oryza sativa Japonica* Group cDNA claone:001-122-C04, full insert sequence, Genbank: AK063844.1, Dec. 4, 2008.
UniProtKB—Q10NA2 (Q10NA2_ORYSJ), UniProt, Aug. 22, 2006.
Antoine et al. "The Rice Homolog of the Sodium/Lithium Tolerance Gene Functions as Molecular Chaperon In Vitro" Physiologia Plantarum, vol. 125, pp. 299-310, Dec. 31, 2005.
Matsumoto et al. "Tobacco and *Arabidopsis* SLT1 Mediate Salt Tolerance of Yeast" Plant Molecular Biology, vol. 45, pp. 489-500, Dec. 31, 2001.

* cited by examiner

*Primary Examiner* — Bratislav Stankovic
*Assistant Examiner* — Wayne Zhong

(57) ABSTRACT

The disclosure discloses isolated polynucleotides and polypeptides, and recombinant DNA constructs useful for conferring improved tolerance in plants to insect pests; compositions (such as plants or seeds) comprising these recombinant DNA constructs; and methods utilizing these recombinant DNA constructs. The recombinant DNA constructs comprise a polynucleotide operably linked to a promoter that is functional in a plant, wherein the polynucleotides encode insect tolerance polypeptides.

9 Claims, No Drawings

Specification includes a Sequence Listing.

PLANTS HAVING ENHANCED TOLERANCE TO INSECT PESTS AND RELATED CONSTRUCTS AND METHODS INVOLVING INSECT TOLERANCE GENES

FIELD

This disclosure relates to the field of plant breeding and genetics and, in particular, relates to recombinant DNA constructs useful for conferring tolerance to insect pests, and methods for control of insect infestation in plants.

BACKGROUND

Numerous insect species are serious pests to common agricultural crops such as corn, soybean, pea, cotton, rice and similar food and fiber crops. Pests' infestation can cause a huge financial loss annually either in crop loss or in purchasing expensive pesticides to keep check on pests. During the last centuries, the primary method of controlling such pests has been through the application of synthetic chemical insecticidal compounds. However, the widespread use of chemical compounds poses many problems with regard to the environment because of the non-selectivity of the compounds and the development of insect resistance to the chemicals.

Advances in biotechnology in the last decades have presented new opportunities for pest control through genetic engineering. In particular, advances in plant genetics coupled with the identification of insect growth factors and naturally-occurring plant defensive compounds or agents offer the opportunity to create transgenic crop plants capable of producing such defensive agents and thereby protect the plants against insect attack.

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Transgenic plants that are resistant to specific insect pests have been produced using genes encoding *Bacillus thuringiensis* (Bt) endotoxins or plant protease inhibitors (PIs). For example, corn and cotton plants have been genetically engineered to produce pesticidal proteins isolated from strains of Bt. These genetically engineered crops are now widely used in agriculture and have provided the farmer with an environmentally friendly and commercially attractive alternative to traditional insect control methods. Generally speaking, the use of biopesticides presents a lower risk of pollution and environmental hazards and biopesticides provide greater target specificity than traditional broad spectrum chemical insecticides. In addition, biopesticides often cost less to produce and thus improve economic yield for a wide variety of crops.

While biopesticides have proven to be very successful commercially, these genetically engineered, insect-resistant crop plants provide resistance to only a narrow range of the economically important insect pests. In some cases, insects can develop resistance to different insecticidal compounds, which raises the need to identify alternative biological control agents for pest control. Accordingly, there remains a need for new pesticidal proteins with different ranges of insecticidal activity against insect pests, e.g., insecticidal proteins which are active against a variety of insects in the order Lepidoptera and the order Coleoptera including but not limited to insect pests that have developed resistance to existing insecticides.

SUMMARY

The following embodiments are among those encompassed by the disclosure:

In one aspect, the present disclosure includes an isolated polynucleotide enhancing insect tolerance of a plant through increasing expression, comprising: (a) a polynucleotide with a nucleotide sequence of at least 85% identity to SEQ ID NO: 4, 7 or 10; (b) a polynucleotide with a nucleotide sequence of at least 85% identity to SEQ ID NO: 5, 8 or 11; (c) a polynucleotide encoding a polypeptide with an amino acid sequence of at least 90% identity to SEQ ID NO: 6, 9 or 12; or (d) the full complement of the nucleotide sequence of (a), (b) or (c). The isolated polynucleotide comprises the nucleotide sequence of SEQ ID NO: 4, SEQ ID NO: 5, SEQ ID NO: 7, SEQ ID NO: 8, SEQ ID NO: 10 or SEQ ID NO: 11. The isolated polynucleotide encodes a polypeptide comprising the amino acid sequence of SEQ ID NO: 6, SEQ ID NO: 9 or SEQ ID NO: 12. The insect pest is a Lepidopteran, particularly Asian Corn Borer (*Ostrinia furnacalis*), Rice Stem Borer (*Chilo suppressalis*), or Oriental Armyworm (*Mythimna separata*).

In another aspect, the present disclosure includes a recombinant DNA construct comprising the isolated polynucleotide operably linked to at least one regulatory element, wherein the polynucleotide comprises (a) a polynucleotide with a nucleotide sequence of at least 85% identity to SEQ ID NO: 4, 5, 7, 8, 10 or 11; (b) a polynucleotide encoding a polypeptide with an amino acid sequence of at least 90% identity to SEQ ID NO: 6, 9 or 12; or (c) the full complement of the nucleotide sequence of (a) or (b). In some aspects the regulatory element is a promoter functional in a plant. The isolated polynucleotide encodes a SLT1, DN-ITP6 or DN-ITP7 polypeptide.

In another aspect, the present disclosure includes a plant, plant cell or seed comprising a recombinant DNA construct comprising the polynucleotide operably linked to at least one regulatory element, wherein the polynucleotide comprises (a) a polynucleotide with a nucleotide sequence of at least 85% identity to SEQ ID NO: 4, 5, 7, 8, 10 or 11; (b) a polynucleotide encoding a polypeptide with an amino acid sequence of at least 90% identity to SEQ ID NO: 6, 9 or 12; or (c) the full complement of the nucleotide sequence of (a) or (b).

In another aspect, the present disclosure includes a plant or plant cell comprising in its genome a recombinant DNA construct comprising a polynucleotide operably linked to at least one regulatory element, wherein the polynucleotide comprises (a) a polynucleotide with a nucleotide sequence of at least 85% identity to SEQ ID NO: 4, 5, 7, 8, 10 or 11; (b) a polynucleotide encoding a polypeptide with an amino acid sequence of at least 90% identity to SEQ ID NO: 6, 9 or 12; or (c) the full complement of the nucleotide sequence of (a) or (b); wherein the plant exhibits increased tolerance to an insect pest when compared to a control plant. The increased insect pest tolerance is created or enhanced against any species of the orders selected from the group consisting of orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera. The insect pest is Asian Corn Borer (*Ostrinia furnacalis*), Rice Stem Borer (*Chilo suppressalis*), or Oriental Armyworm (*Mythimna separata*). The present disclosure includes any of the plants of the disclosure, wherein the plant is selected from the group consisting of rice, maize, soybean, sunflower, sorghum, canola, wheat, alfalfa, cotton, barley, millet, sugar cane and switchgrass.

In another aspect, methods of increasing tolerance in a plant to an insect pest are provided, the methods comprise increasing expression of at least one polynucleotide encoding a SLT1, DN-ITP6 or DN-ITP7 polypeptide, wherein the polynucleotide comprises: (a) a polynucleotide with a nucleotide sequence of at least 85% identity to SEQ ID NO: 4, 7 or 10; (b) a polynucleotide with a nucleotide sequence of at least 85% identity to SEQ ID NO: 5, 8 or 11; and (c) a polynucleotide encoding a polypeptide with an amino acid sequence of at least 90% identity to SEQ ID NO: 6, 9 or 12. The methods of increasing tolerance in a plant to an insect pest comprise: (a) introducing into a regenerable plant cell a recombinant DNA construct comprising a polynucleotide operably linked to at least one regulatory element, wherein the polynucleotide encodes a polypeptide having an amino acid sequence of at least 90% identity compared to SEQ ID NO: 6, 9 or 12; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein the progeny plant comprises in its genome the recombinant DNA construct and exhibits increased tolerance to an insect pest when compared to a control plant not comprising the recombinant DNA construct. The insect pest is a Lepidopteran, particularly Asian Corn Borer (*Ostrinia furnacalis*), Rice Stem Borer (*Chilo suppressalis*), or Oriental Armyworm (*Mythimna separata*).

In another aspect, methods are provided for evaluating tolerance in a plant to an insect pest, comprising: (a) introducing into a regenerable plant cell a recombinant DNA construct comprising a polynucleotide operably linked to at least one regulatory element, wherein the polynucleotide encodes a polypeptide having an amino acid sequence of at least 90% identity when compared to SEQ ID NO: 6, 9 or 12; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for tolerance to an insect pest compared to a control plant not comprising the recombinant DNA construct. The insect pest is a Lepidopteran, particularly Asian Corn Borer (*Ostrinia furnacalis*), Rice Stem Borer (*Chilo suppressalis*), or Oriental Armyworm (*Mythimna separata*).

In another aspect, the present disclosure concerns a recombinant DNA construct comprising any of the isolated polynucleotides of the present disclosure operably linked to at least one heterologous regulatory element, and a cell, a plant, and a seed comprising the recombinant DNA construct. The cell may be eukaryotic, e.g., a yeast, insect or plant cell, or prokaryotic, e.g., a bacterium.

BRIEF DESCRIPTION OF THE SEQUENCE LISTINGS

The disclosure can be more fully understood from the following detailed description and the accompanying Sequence Listing which forms part of the application.

TABLE 1

SEQ ID NOs for nucleotide and amino acid sequences provided in the sequence listing

| Source species | Clone Designation | SEQ ID NO: (Nucleotide) | SEQ ID NO: (Amino Acid) |
| --- | --- | --- | --- |
| *Oryza sativa* | T-DNA flanking sequence in AH35009 (RB) | 1 | n/a |
| *Oryza sativa* | T-DNA flanking sequence in AH35009 (LB) | 2 | n/a |
| *Oryza sativa* | T-DNA flanking sequence in AH30161 (LB) | 3 | n/a |
| *Oryza sativa* | OsSLT1 | 4, 5 | 6 |
| *Oryza sativa* | OsDN-ITP6 | 7, 8 | 9 |
| *Oryza sativa* | OsDN-ITP7 | 10, 11 | 12 |
| Artificial sequence | Primers | 13-24 | n/a |

The sequence descriptions and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. § 1.822. The official copy of the sequence listing is submitted electronically via EFS-Web as an ASCII formatted sequence listing with a file named RTS22593k-US-PCT SequenceListing.txt created on 15 Jul. 2020 and having a size of 19.2 kilobytes and is filed concurrently with the specification. The sequence listing comprised in this ASCII formatted document is part of the specification and is herein incorporated by reference in its entirety.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

As used herein:

The term "OsSLT1" is SLT1 protein that confers increased tolerance to an insect pest and is encoded by the rice gene locus LOC_Os03g16910.1. "SLT1 polypeptide" refers herein to the OsSLT1 polypeptide and its homologs from other organisms.

The OsSLT1 polypeptide (SEQ ID NO: 6) is encoded by the coding sequence (CDS) (SEQ ID NO: 5) or nucleotide sequence (SEQ ID NO: 4) at rice gene locus LOC_Os03g16910.1. This polypeptide is annotated as "SLT1 protein, putative, expressed" in TIGR (the internet at plant biology msu.edu/index.shtml), and in NCBI (on the world web at ncbi.nlm.nih.gov), however does not have any prior assigned function.

The term "OsDN-ITP6" is an insect tolerance protein 6 that confers increased tolerance to an insect pest and is encoded by the rice gene locus LOC_Os01g53730.1. "DN- ITP6 polypeptide" refers herein to the OsDN-ITP6 polypeptide and its homologs from other organisms.

The OsDN-ITP6 polypeptide (SEQ ID NO: 9) is encoded by the coding sequence (CDS) (SEQ ID NO: 8) or nucleotide sequence (SEQ ID NO: 7) at rice gene locus LOC_Os01g53730.1. This polypeptide is annotated as "expressed protein" in TIGR, however does not have any prior assigned function.

The term "OsDN-ITP7" is an insect tolerance protein 7 that confers increased tolerance to an insect pest and is encoded by the rice gene locus LOC_Os09g10010.1. "DN-ITP7 polypeptide" refers herein to the OsDN-ITP7 polypeptide and its homologs from other organisms.

The OsDN-ITP7 polypeptide (SEQ ID NO: 12) is encoded by the coding sequence (CDS) (SEQ ID NO: 11) or nucleotide sequence (SEQ ID NO: 10) at rice gene locus LOC_Os09g10010.1. This polypeptide is annotated as "expressed protein" in TIGR, however does not have any prior assigned function.

The term "insect tolerance protein" is used herein to refer to a polypeptide that inhibits the growth of, stunts the growth of, and/or kills one or more insect pests, including, but not limited to, members of the Lepidoptera, Diptera, Hemiptera and Coleoptera orders.

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control" or "control plant" or "control plant cell" provides a reference point for measuring changes in phenotype of a subject plant or plant cell which was genetically altered by, such as transformation, and has been affected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to a condition or stimulus that would induce expression of the gene of interest; or (e) the subject plant or plant cell itself, under conditions in which the gene of interest is not expressed.

In this disclosure, ZH11-TC and empty vector plants indicate control plants. ZH11-TC represents rice plants generated from tissue cultured Zhonghua 11, and empty vector represents plants transformed with empty vector DP0158.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Modified plant" includes reference to a plant which comprises within its genome a heterologous polynucleotide or modified gene or promoter. The heterologous polynucleotide can be stably integrated within the genome such that the polynucleotide is passed on to successive generations. The heterologous polynucleotide may be integrated into the genome alone or as part of a recombinant DNA construct. A T0 plant is directly recovered from the transformation and regeneration process. Progeny of T0 plants are referred to as T1 (first progeny generation), T2 (second progeny generation), etc. The modified gene or promoter may be insertion or deletion of a single or several or a fragment of deoxy nucleotide in the plant genome.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product has been removed.

"Precursor" protein refers to the primary product of translation of mRNA; i.e., with pre- and/or pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a cDNA. In some embodiments the non-genomic nucleic acid molecule is a synthetic nucleic acid sequence.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" and "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632). A "mitochondrial signal peptide" is an amino acid sequence which directs a precursor protein into the mitochondria (Zhang and Glaser (2002) *Trends Plant Sci* 7:14-21).

Sequence alignments and percent identity calculations may be determined using a variety of comparison methods designed to detect homologous sequences including, but not limited to, the MEGALIGN® program of the LASER-GENE® bioinformatics computing suite (DNASTAR® Inc., Madison, Wis.). Unless stated otherwise, multiple alignment of the sequences provided herein were performed using the Clustal V method of alignment (Higgins and Sharp, CAB/OS. 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to the embodiments:

Embodiments include isolated polynucleotides and polypeptides, recombinant DNA constructs useful for conferring insect tolerance, compositions (such as plants or seeds) comprising these recombinant DNA constructs, and methods utilizing these recombinant DNA constructs.

Isolated Polynucleotides and Polypeptides

The present disclosure includes the following isolated polynucleotides and polypeptides:

In some embodiments, polynucleotides are provided encoding SLT1, DN-ITP6 or DN-ITP7 polypeptides.

In some embodiments, isolated polynucleotides are provided comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, when compared to SEQ ID NO: 6, 9 or 12; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure.

In some embodiments, isolated polypeptides are provided having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity when compared to SEQ ID NO: 6, 9 or 12. The polypeptides are insect tolerance polypeptide SLT1, DN-ITP6 or DN-ITP7.

In some embodiments, isolated polynucleotide are provided comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, when compared to SEQ ID NO: 4, 5, 7, 8, 10 or 11; or (ii) a full complement of the nucleic acid sequence of (i). Any of the foregoing isolated polynucleotides may be utilized in any recombinant DNA constructs of the present disclosure. The isolated polynucleotide preferably encodes an insect tolerance protein. Increasing expression of this polypeptide increases plant tolerance to an insect pest.

Recombinant DNA Constructs

In one aspect, the present disclosure includes recombinant DNA constructs.

In one embodiment, a recombinant DNA construct comprises a polynucleotide operably linked to at least one regulatory element (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, when compared to SEQ ID NO: 6, 9 or 12; or (ii) a full complement of the nucleic acid sequence of (i).

In another embodiment, a recombinant DNA construct comprises a polynucleotide operably linked to at least one regulatory element (e.g., a promoter functional in a plant), wherein the polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, when compared to SEQ ID NO: 4, 5, 7, 8, 10 or 11; or (ii) a full complement of the nucleic acid sequence of (i).

In another embodiment, a recombinant DNA construct comprises a polynucleotide operably linked to at least one regulatory element (e.g., a promoter functional in a plant), wherein the polynucleotide encodes a SLT1, DN-ITP6 or DN-ITP7 protein. These polypeptides provide tolerance to an insect pest activity, and may be from, for example, *Oryza sativa, Oryza australiensis, Oryza barthii, Oryza glaberrima* (African rice), *Oryza latifolia, Oryza longistaminata, Oryza meridionalis, Oryza officinalis, Oryza punctata, Oryza rufipogon* (brownbeard or red rice), *Oryza nivara* (Indian wild rice), *Arabidopsis thaliana*, *Zea mays*, *Glycine max*, *Glycine tabacina*, *Glycine soja* or *Glycine tomentella*.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Regulatory Elements:

A recombinant DNA construct of the present disclosure may comprise at least one regulatory element.

A regulatory element may be a promoter or enhancer.

A number of promoters can be used in recombinant DNA constructs of the present disclosure. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High level, constitutive expression of the candidate gene under control of the 35S or UBI promoter may (or may not) have pleiotropic effects, although candidate gene efficacy may be estimated when driven by a constitutive promoter. Use of tissue-specific and/or stress-specific promoters may eliminate undesirable effects, but retain the ability to enhance insect tolerance. This type of effect has been observed in *Arabidopsis* for drought and cold tolerance (Kasuga et al., *Nature Biotechnol.* 17:287-91 (1999)).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the disclosure, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present disclosure which causes the desired temporal and spatial expression.

Promoters which are seed or embryo-specific and may be useful in the disclosure include soybean Kunitz trypsin inhibitor (Kti3, Jofuku and Goldberg, *Plant Cell* 1:1079-1093 (1989)), patatin (potato tubers) (Rocha-Sosa, M., et al., *EMBO J.* 8:23-29 (1989)), convicilin, vicilin, and legumin (pea cotyledons) (Rerie, W. G., et al., *Mol. Gen. Genet.* 259:149-157 (1991); Newbigin, E. J., et al., *Planta* 180:461-470 (1990); Higgins, T. J. V., et al., *Plant. Mol. Biol.* 11:683-695 (1988)), zein (maize endosperm) (Schemthaner, J. P., et al., *EMBO J.* 7:1249-1255 (1988)), phaseolin (bean cotyledon) (Segupta-Gopalan, C., et al., *Proc. Natl. Acad. Sci. U.S.A.* 82:3320-3324 (1995)), phytohemagglutinin (bean cotyledon) (Voelker, T. et al., *EMBO J.* 6:3571-3577 (1987)), B-conglycinin and glycinin (soybean cotyledon) (Chen, Z-L, et al., *EMBO J.* 7:297-302 (1988)), glutelin (rice endosperm), hordein (barley endosperm) (Marris, C., et al., *Plant Mol. Biol.* 10:359-366 (1988)), glutenin and gliadin (wheat endosperm) (Colot, V., et al., *EMBO J.* 6:3559-3564 (1987)), and sporamin (sweet potato tuberous root) (Hattori, T., et al., *Plant Mol. Biol.* 14:595-604 (1990)). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., *Bio/Technology* 7: L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J.* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in the current disclosure include the following: 1) the stress-inducible RD29A promoter (Kasuga et al., *Nature Biotechnol.* 17:287-91 (1999)); 2) the barley promoter, B22E; expression of B22E is specific to the pedicel in developing maize kernels ("Primary Structure of a Novel Barley Gene Differentially Expressed in Immature Aleurone Layers", Klemsdal et al., *Mol. Gen. Genet.* 228 (1/2):9-16 (1991)); and 3) maize promoter, Zag2 ("Identification and molecular characterization of ZAG1, the maize homolog of the *Arabidopsis* floral homeotic gene AGAMOUS", Schmidt et al., *Plant Cell* 5(7):729-737 (1993); "Structural characterization, chromosomal localization and phylogenetic evaluation of two pairs of AGAMOUS-like MADS-box genes from maize", Theissen et al., *Gene* 156 (2):155-166 (1995); NCBI GenBank Accession No. X80206)). Zag2 transcripts can be detected five days prior to pollination to seven to eight days after pollination ("DAP"), and directs expression in the carpel of developing female inflorescences and CimI which is specific to the nucleus of developing maize kernels. CimI transcript is detected four to five days before pollination to six to eight DAP. Other useful promoters include any promoter which can be derived from a gene whose expression is maternally associated with developing female florets.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all of its final mass, and various storage products (i.e., starch, protein, oil) are produced. Finally, the maturation phase occurs from about 40 DAP to harvest. During this phase of kernel development, the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, Cim1 that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp (WO 00/12733), herein incorporated by reference. Additional early kernel/embryo promoters that find use in certain methods of the present disclosure include the seed-preferred promoter/tp2 (U.S. Pat. No. 5,525,716); maize Zm40 promoter (U.S. Pat. No. 6,403,862); maize nuc1c (U.S. Pat. No. 6,407,315); maize ckx1-2 promoter (U.S. Pat. No. 6,921,815 and US Patent Application Publication Number 2006/0037103); maize lec1 promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007). Additional promoters for regulating the expression of the nucleotide sequences of the present disclosure in plants are stalk-specific promoters. Such stalk-specific promoters include the alfalfa S2A promoter (GenBank Accession No. EF030816; Abrahams et al., *Plant Mol. Biol.* 27:513-528 (1995)) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (GenBank Accession No. EF030817), and the constitutive promoter GOS2 from *Zea mays*. Other promoters include root preferred promoters, such as the maize NAS2 promoter, the maize Cyclo promoter (US Publication No. 2006/0156439, published Jul. 13, 2006), the maize ROOTMET2 promoter (WO 2005/063998, published Jul. 14, 2005), the CR1BIO promoter (WO 2006/055487, published May 26, 2006), the CRWAQ81 promoter (WO 2005/035770, published Apr. 21, 2005) and the maize ZRP2.47 promoter (NCBI Accession No. U38790; NCBI GI No. 1063664).

Recombinant DNA constructs of the present disclosure may also include other regulatory sequences including, but not limited to, translation leader sequences, introns, and polyadenylation recognition sequences. In another embodiment of the present disclosure, a recombinant DNA construct of the present disclosure further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395-4405 (1988); Callis et al., *Genes Dev.* 1:1183-1200 (1987)).

An enhancer or enhancer element refers to a cis-acting transcriptional regulatory element, a.k.a. cis-element, which confers an aspect of the overall expression pattern, but is usually insufficient alone to drive transcription, of an operably linked polynucleotide sequence. An isolated enhancer element may be fused to a promoter to produce a chimeric promoter cis-element, which confers an aspect of the overall modulation of gene expression. Enhancers are known in the art and include the SV40 enhancer region, the CaMV 35S enhancer element, and the like. Some enhancers are also known to alter normal regulatory element expression patterns, for example, by causing a regulatory element to be expressed constitutively when without the enhancer, the same regulatory element is expressed only in one specific tissue or a few specific tissues. Duplicating the upstream region of the CaMV35S promoter has been shown to increase expression by approximately tenfold (Kay, R. et al., (1987) Science 236: 1299-1302).

Enhancers for use in the current disclosure may include CaMV 35S (Benfey, et al., (1990) EMBO J. 9:1685-96); 4×B3 P-CaMV.35S Enhancer Domain—four tandem copies of the B3 domain (208 to 155) as described in U.S. Pat. No. 5,097,025; 4×AS-1 P-CaMV.35S Enhancer Domain—four tandem copies of the "activation sequence" (83 to 62) as described in U.S. Pat. No. 5,097,025; 2×B1-B2 P-CaMV.35S Enhancer Domain—two tandem copies of the B1-B2 domain (148 to 90) as described in U.S. Pat. No. 5,097,025; 2×A1-B3 P-CaMV.35S Enhancer Domain—two tandem copies of the A1-B3 domain (208 to 46) as described in U.S. Pat. No. 5,097,025; 2×B1-B5 P-CaMV.35S Enhancer Domain—two tandem copies of the B1-B5 domain (343 to 90) as described in U.S. Pat. No. 5,097,025; the omega enhancer or the omega prime enhancer (Gallie, et al., (1989) Molecular Biology of RNA ed. Cech (Liss, New York) 237-256 and Gallie, et al., (1987) Gene 60:217-25), the enhancers of U.S. Pat. No. 7,803,992, the sugarcane bacilliform viral (SCBV) enhancer element (WO2013130813).

Any plant can be selected for the identification of regulatory sequences and genes to be used in recombinant DNA constructs of the present disclosure. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castor bean, cauliflower, celery, cherry, chicory, cilantro, citrus, clementines, clover, coconut, coffee, corn, cotton, cranberry, cucumber, Douglas fir, eggplant, endive, escarole, *eucalyptus*, fennel, figs, garlic, gourd, grape, grapefruit, honey dew, jicama, kiwifruit, lettuce, leeks, lemon, lime, Loblolly pine, linseed, maize, mango, melon, mushroom, nectarine, nut, oat, oil palm, oil seed rape, okra, olive, onion, orange, an ornamental plant, palm, *papaya*, parsley, parsnip, pea, peach, peanut, pear, pepper, persimmon, pine, pineapple, plantain, plum, pomegranate, poplar, potato, pumpkin, quince, *radiata* pine, radicchio, radish, rapeseed, raspberry, rice, rye, sorghum, Southern pine, soybean, spinach, squash, strawberry, sugar beet, sugarcane, sunflower, sweet potato, sweet gum, tangerine, tea, tobacco, tomato, triticale, turf, turnip, a vine, watermelon, wheat, yams, and zucchini.

Compositions

A composition of the present disclosure is a plant comprising in its genome any of the recombinant DNA constructs of the present disclosure (such as any of the constructs discussed above). Compositions also include any progeny of the plant, and any seed obtained from the plant or its progeny, wherein the progeny or seed comprises within its genome the recombinant DNA construct. Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct. These seeds can be grown to produce plants that would exhibit an altered agronomic characteristic, or used in a breeding program to produce hybrid seed, which can be grown to produce plants that would exhibit such an altered agronomic characteristic. The seeds may be maize seeds, or rice seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley or millet.

The recombinant DNA construct is stably integrated into the genome of the plant.

Embodiments include but are not limited to the following:

1. A transgenic plant (for example, a rice, maize or soybean plant) comprising in its genome a recombinant DNA construct comprising a polynucleotide operably linked to at least one heterologous regulatory element, wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, when compared to SEQ ID NO: 6, 9 or 12; and wherein the transgenic plant exhibits increased tolerance to an insect pest when compared to a control plant not comprising the recombinant DNA construct.

2. The transgenic plant of embodiment 1, wherein the polynucleotide encodes a SLT1, DN-ITP6 or DN-ITP7 polypeptide, for example, from *Oryza sativa, Oryza australiensis, Oryza barthii, Oryza glaberrima* (African rice), *Oryza latifolia, Oryza longistaminata, Oryza meridionalis, Oryza officinalis, Oryza punctata, Oryza rufipogon* (brownbeard or red rice), *Oryza nivara* (Indian wild rice), *Arabidopsis thaliana, Cicer arietinum, Solanum tuberosum, Brassica oleracea, Zea mays, Glycine max, Glycine tabacina, Glycine soja* or *Glycine tomentella*.

3. The transgenic plant of any one of embodiments 1 to 2, wherein the transgenic plant further comprises at least one polynucleotide encoding an insecticidal polypeptide.

4. The transgenic plant of any one of embodiments 1 to 2, wherein the transgenic plant further comprises at least one recombinant polynucleotide encoding a polypeptide of interest.

5. Any progeny of the above plants in embodiments 1-4, any seeds of the above plants in embodiments 1-4, any seeds of progeny of the above plants in embodiments 1-4, and cells from any of the above plants in embodiments 1-4 and progeny thereof.

In any of the foregoing embodiments 1-5 or any other embodiments of the present disclosure, the recombinant DNA construct may comprise at least one heterologous promoter functional in a plant as a regulatory element.

By "insecticidal protein" is used herein to refer to a polypeptide that has toxic activity against one or more insect pests, including, but not limited to, members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., *Xenorhabdus* sp., *Clostridium bifermentans* and *Paenibacillus popilliae*. Pesticidal proteins include but are not limited to: insecticidal proteins from *Pseudomonas* sp. such as PSEEN3174 (Monalysin; (2011) PLoS Pathogens 7:1-13); from *Pseudomonas protegens* strain CHAO and Pf-5 (previously *fluorescens*) (Pechy-Tarr, (2008) *Environmental Microbiology* 10:2368-2386; GenBank Accession No. EU400157); from *Pseudomonas Taiwanensis* (Liu, et al., (2010) *J. Agric. Food Chem.,* 58:12343-12349) and from *Pseudomonas* pseudoalcligenes (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxicology Journal,* 3:101-118 and Morgan, et al., (2001) *Applied and Envir. Micro.* 67:2062-2069); U.S. Pat. Nos. 6,048,838, and 6,379,946; a PIP-1 polypeptide of US publication number US2014008054; an AfIP-1A and/or AfIP-1B polypeptide of U.S. Ser. No. 13/800,233; a PHI-4 polypeptide of U.S. Ser. No. 13/839,702; and 5-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry 29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry51, Cry55, Cry56, Cry57, Cry58, Cry59, Cry60, Cry61, Cry62, Cry63, Cry64, Cry65, Cry66, Cry67, Cry68, Cry69, Cry70, Cry71 and Cry72 classes of δ-endotoxin genes and the *B. thuringiensis* cytolytic cyt1 and cyt2 genes. Members of these classes of *B. thuringiensis* insecticidal proteins include, but are not limited to Cry1Aa1 (Accession #AAA22353); Cry1Aa2 (Accession #Accession #AAA22552); Cry1Aa3 (Accession #BAA00257); Cry1Aa4 (Accession #CAA31886); Cry1Aa5 (Accession #BAA04468); Cry1Aa6 (Accession #AAA86265);

Cry1Aa7 (Accession #AAD46139); Cry1Aa8 (Accession #126149); Cry1Aa9 (Accession #BAA77213); Cry1Aa10 (Accession #AAD55382); Cry1Aa11 (Accession #CAA70856); Cry1Aa12 (Accession #AAP80146); Cry1Aa13 (Accession #AAM44305); Cry1Aa14 (Accession #AAP40639); Cry1Aa15 (Accession #AAY66993); Cry1Aa16 (Accession #HQ439776); Cry1Aa17 (Accession #HQ439788); Cry1Aa18 (Accession #HQ439790); Cry1Aa19 (Accession #HQ685121); Cry1Aa20 (Accession #JF340156); Cry1Aa21 (Accession #JN651496); Cry1Aa22 (Accession #KC158223); Cry1Ab1 (Accession #AAA22330); Cry1Ab2 (Accession #AAA22613); Cry1Ab3 (Accession #AAA22561); Cry1Ab4 (Accession #BAA00071); Cry1Ab5 (Accession #CAA28405); Cry1Ab6 (Accession #AAA22420); Cry1Ab7 (Accession #CAA31620); Cry1Ab8 (Accession #AAA22551); Cry1Ab9 (Accession #CAA38701); Cry1Ab10 (Accession #A29125); Cry1Ab11 (Accession #112419); Cry1Ab12 (Accession #AAC64003); Cry1Ab13 (Accession #AAN76494); Cry1Ab14 (Accession #AAG16877); Cry1Ab15 (Accession #AAO13302); Cry1Ab16 (Accession #AAK55546); Cry1Ab17 (Accession #AAT46415); Cry1Ab18 (Accession #AAQ88259); Cry1Ab19 (Accession #AAW31761); Cry1Ab20 (Accession #ABB72460); Cry1Ab21 (Accession #ABS18384); Cry1Ab22 (Accession #ABW87320); Cry1Ab23 (Accession #HQ439777); Cry1Ab24 (Accession #HQ439778); Cry1Ab25 (Accession #HQ685122); Cry1Ab26 (Accession #HQ847729); Cry1Ab27 (Accession #JN135249); Cry1Ab28 (Accession #JN135250); Cry1Ab29 (Accession #JN135251); Cry1Ab30 (Accession #JN135252); Cry1Ab31 (Accession #JN135253); Cry1Ab32 (Accession #JN135254); Cry1Ab33 (Accession #AAS93798); Cry1Ab34 (Accession #KC156668); Cry1Ab-like (Accession #AAK14336); Cry1Ab-like (Accession #AAK14337); Cry1Ab-like (Accession #AAK14338); Cry1Ab-like (Accession #ABG88858); Cry1Ac1 (Accession #AAA22331); Cry1Ac2 (Accession #AAA22338); Cry1Ac3 (Accession #CAA38098); Cry1Ac4 (Accession #AAA73077); Cry1Ac5 (Accession #AAA22339); Cry1Ac6 (Accession #AAA86266); Cry1Ac7 (Accession #AAB46989); Cry1Ac8 (Accession #AAC44841); Cry1Ac9 (Accession #AAB49768); Cry1Ac10 (Accession #CAA05505); Cry1Ac11 (Accession #CAA10270); Cry1Ac12 (Accession #112418); Cry1Ac13 (Accession #AAD38701); Cry1Ac14 (Accession #AAQ06607); Cry1Ac15 (Accession #AAN07788); Cry1Ac16 (Accession #AAU87037); Cry1Ac17 (Accession #AAX18704); Cry1Ac18 (Accession #AAY88347); Cry1Ac19 (Accession #ABD37053); Cry1Ac20 (Accession #ABB89046); Cry1Ac21 (Accession #AAY66992); Cry1Ac22 (Accession #ABZ01836); Cry1Ac23 (Accession #CAQ30431); Cry1Ac24 (Accession #ABL01535); Cry1Ac25 (Accession #FJ513324); Cry1Ac26 (Accession #FJ617446); Cry1Ac27 (Accession #FJ617447); Cry1Ac28 (Accession #ACM90319); Cry1Ac29 (Accession #DQ438941); Cry1Ac30 (Accession #GQ227507); Cry1Ac31 (Accession #GU446674); Cry1Ac32 (Accession #HM061081); Cry1Ac33 (Accession #GQ866913); Cry1Ac34 (Accession #HQ230364); Cry1Ac35 (Accession #JF340157); Cry1Ac36 (Accession #JN387137); Cry1Ac37 (Accession #JQ317685); Cry1Ad1 (Accession #AAA22340); Cry1Ad2 (Accession #CAA01880); Cry1Ae1 (Accession #AAA22410); Cry1Af1 (Accession #AAB82749); Cry1Ag1 (Accession #AAD46137); Cry1Ah1 (Accession #AAQ14326); Cry1Ah2 (Accession #ABB76664); Cry1Ah3 (Accession #HQ439779); Cry1Ai1 (Accession #AAO39719); Cry1Ai2 (Accession #HQ439780); Cry1A-like (Accession #AAK14339); Cry1Ba1 (Accession #CAA29898); Cry1Ba2 (Accession #CAA65003); Cry1Ba3 (Accession #AAK63251); Cry1Ba4 (Accession #AAK51084); Cry1Ba5 (Accession #AB020894); Cry1Ba6 (Accession #ABL60921); Cry1Ba7 (Accession #HQ439781); Cry1Bb1 (Accession #AAA22344); Cry1Bb2 (Accession #HQ439782); Cry1Bc1 (Accession #CAA86568); Cry1Bd1 (Accession #AAD10292); Cry1Bd2 (Accession #AAM93496); Cry1Be1 (Accession #AAC32850); Cry1Be2 (Accession #AAQ52387); Cry1Be3 (Accession #ACV96720); Cry1Be4 (Accession #HM070026); Cry1Bf1 (Accession #CAC50778); Cry1Bf2 (Accession #AAQ52380); Cry1Bg1 (Accession #AAO39720); Cry1Bh1 (Accession #HQ589331); Cry1Bi1 (Accession #KC156700); Cry1Ca1 (Accession #CAA30396); Cry1Ca2 (Accession #CAA31951); Cry1Ca3 (Accession #AAA22343); Cry1Ca4 (Accession #CAA01886); Cry1Ca5 (Accession #CAA65457); Cry1Ca6 [1](Accession #AAF37224); Cry1Ca7 (Accession #AAG50438); Cry1Ca8 (Accession #AAM00264); Cry1Ca9 (Accession #AAL79362); Cry1Ca10 (Accession #AAN16462); Cry1Ca11 (Accession #AAX53094); Cry1Ca12 (Accession #HM070027); Cry1Ca13 (Accession #HQ412621); Cry1Ca14 (Accession #JN651493); Cry1Cb1 (Accession #M97880); Cry1Cb2 (Accession #AAG35409); Cry1Cb3 (Accession #ACD50894); Cry1 Cb-like (Accession #AAX63901); Cry1Da1 (Accession #CAA38099); Cry1Da2 (Accession #176415); Cry1Da3 (Accession #HQ439784); Cry1db1 (Accession #CAA80234); Cry1db2 (Accession #AAK48937); Cry1Dc1 (Accession #ABK35074); Cry1Ea1 (Accession #CAA37933); Cry1Ea2 (Accession #CAA39609); Cry1Ea3 (Accession #AAA22345); Cry1Ea4 (Accession #AAD04732); Cry1Ea5 (Accession #A15535); Cry1Ea6 (Accession #AAL50330); Cry1Ea7 (Accession #AAW72936); Cry1Ea8 (Accession #ABX11258); Cry1Ea9 (Accession #HQ439785); Cry1Ea10 (Accession #ADR00398); Cry1Ea11 (Accession #JQ652456); Cry1Eb1 (Accession #AAA22346); Cry1Fa1 (Accession #AAA22348); Cry1Fa2 (Accession #AAA22347); Cry1Fa3 (Accession #HM070028); Cry1Fa4 (Accession #HM439638); Cry1Fb1 (Accession #CAA80235); Cry1Fb2 (Accession #BAA25298); Cry1Fb3 (Accession #AAF21767); Cry1Fb4 (Accession #AAC10641); Cry1Fb5 (Accession #AAO13295); Cry1Fb6 (Accession #ACD50892); Cry1Fb7 (Accession #ACD50893); Cry1Ga1 (Accession #CAA80233); Cry1Ga2 (Accession #CAA70506); Cry1Gb1 (Accession #AAD10291); Cry1Gb2 (Accession #AAO13756); Cry1Gc1 (Accession #AAQ52381); Cry1Ha1 (Accession #CAA80236); Cry1Hb1 (Accession #AAA79694); Cry1Hb2 (Accession #HQ439786); Cry1H-like (Accession #AAF01213); Cry1Ia1 (Accession #CAA44633); Cry1Ia2 (Accession #AAA22354); Cry1Ia3 (Accession #AAC36999); Cry1Ia4 (Accession #AAB00958); Cry1Ia5 (Accession #CAA70124); Cry1Ia6 (Accession #AAC26910); Cry1Ia7 (Accession #AAM73516); Cry1Ia8 (Accession #AAK66742); Cry1Ia9 (Accession #AAQ08616); Cry1Ia10 (Accession #AAP86782); Cry1Ia11 (Accession #CAC85964); Cry1Ia12 (Accession #AAV53390); Cry1Ia13 (Accession #ABF83202); Cry1Ia14 (Accession #ACG63871); Cry1Ia15 (Accession #FJ617445); Cry1Ia16 (Accession #FJ617448); Cry1Ia17 (Accession #GU989199); Cry1Ia18 (Accession #ADK23801); Cry1Ia19 (Accession #HQ439787); Cry1Ia20 (Accession #JQ228426); Cry1Ia21 (Accession #JQ228424); Cry1Ia22 (Accession #JQ228427); Cry1Ia23

(Accession #JQ228428); Cry1Ia24 (Accession #JQ228429); Cry1Ia25 (Accession #JQ228430); Cry1Ia26 (Accession #JQ228431); Cry1Ia27 (Accession #JQ228432); Cry1Ia28 (Accession #JQ228433); Cry1Ia29 (Accession #JQ228434); Cry1Ia30 (Accession #JQ317686); Cry1Ia31 (Accession #JX944038); Cry1Ia32 (Accession #JX944039); Cry1Ia33 (Accession #JX944040); Cry1Ib1 (Accession #AAA82114); Cry1Ib2 (Accession #ABW88019); Cry1Ib3 (Accession #ACD75515); Cry1 Ib4 (Accession #HM051227); Cry1 Ib5 (Accession #HM070028); Cry1 Ib6 (Accession #ADK38579); Cry1 Ib7 (Accession #JN571740); Cry1 Ib8 (Accession #JN675714); Cry1 Ib9 (Accession #JN675715); Cry1Ib10 (Accession #JN675716); Cry1Ib11 (Accession #JQ228423); Cry1Ic1 (Accession #AAC62933); Cry1 Ic2 (Accession #AAE71691); Cry1Id1 (Accession #AAD44366); Cry1Id2 (Accession #JQ228422); Cry1Ie1 (Accession #AAG43526); Cry1Ie2 (Accession #HM439636); Cry1Ie3 (Accession #KC156647); Cry1Ie4 (Accession #KC156681); Cry1If1 (Accession #AAQ52382); Cry1Ig1 (Accession #KC156701); Cry1I-like (Accession #AAC31094); Cry1I-like (Accession #ABG88859); Cry1Ja1 (Accession #AAA22341); Cry1Ja2 (Accession #HM070030); Cry1Ja3 (Accession #JQ228425); Cry1Jb1 (Accession #AAA98959); Cry1Jc1 (Accession #AAC31092); Cry1Jc2 (Accession #AAQ52372); Cry1Jd1 (Accession #CAC50779); Cry1Ka1 (Accession #AAB00376); Cry1Ka2 (Accession #HQ439783); Cry1La1 (Accession #AAS60191); Cry1La2 (Accession #HM070031); Cry1Ma1 (Accession #FJ884067); Cry1Ma2 (Accession #KC156659); Cry1Na1 (Accession #KC156648); Cry1Nb1 (Accession #KC156678); Cry1-like (Accession #AAC31091); Cry2Aa1 (Accession #AAA22335); Cry2Aa2 (Accession #AAA83516); Cry2Aa3 (Accession #D86064); Cry2Aa4 (Accession #AAC04867); Cry2Aa5 (Accession #CAA10671); Cry2Aa6 (Accession #CAA10672); Cry2Aa7 (Accession #CAA10670); Cry2Aa8 (Accession #AAO13734); Cry2Aa9 (Accession #AAO13750); Cry2Aa10 (Accession #AAQ04263); Cry2Aa11 (Accession #AAQ52384); Cry2Aa12 (Accession #ABI83671); Cry2Aa13 (Accession #ABL01536); Cry2Aa14 (Accession #ACF04939); Cry2Aa15 (Accession #JN426947); Cry2Ab1 (Accession #AAA22342); Cry2Ab2 (Accession #CAA39075); Cry2Ab3 (Accession #AAG36762); Cry2Ab4 (Accession #AAO13296); Cry2Ab5 (Accession #AAQ04609); Cry2Ab6 (Accession #AAP59457); Cry2Ab7 (Accession #AAZ66347); Cry2Ab8 (Accession #ABC95996); Cry2Ab9 (Accession #ABC74968); Cry2Ab10 (Accession #EF157306); Cry2Ab11 (Accession #CAM84575); Cry2Ab12 (Accession #ABM21764); Cry2Ab13 (Accession #ACG76120); Cry2Ab14 (Accession #ACG76121); Cry2Ab15 (Accession #HM037126); Cry2Ab16 (Accession #GQ866914); Cry2Ab17 (Accession #HQ439789); Cry2Ab18 (Accession #JN135255); Cry2Ab19 (Accession #JN135256); Cry2Ab20 (Accession #JN135257); Cry2Ab21 (Accession #JN135258); Cry2Ab22 (Accession #JN135259); Cry2Ab23 (Accession #JN135260); Cry2Ab24 (Accession #JN135261); Cry2Ab25 (Accession #JN415485); Cry2Ab26 (Accession #JN426946); Cry2Ab27 (Accession #JN415764); Cry2Ab28 (Accession #JN651494); Cry2Ac1 (Accession #CAA40536); Cry2Ac2 (Accession #AAG35410); Cry2Ac3 (Accession #AAQ52385); Cry2Ac4 (Accession #ABC95997); Cry2Ac5 (Accession #ABC74969); Cry2Ac6 (Accession #ABC74793); Cry2Ac7 (Accession #CAL18690); Cry2Ac8 (Accession #CAM09325); Cry2Ac9 (Accession #CAM09326); Cry2Ac10 (Accession #ABN15104); Cry2Ac11 (Accession #CAM83895); Cry2Ac12 (Accession #CAM83896); Cry2Ad1 (Accession #AAF09583); Cry2Ad2 (Accession #ABC86927); Cry2Ad3 (Accession #CAK29504); Cry2Ad4 (Accession #CAM32331); Cry2Ad5 (Accession #CAO78739); Cry2Ae1 (Accession #AAQ52362); Cry2Af1 (Accession #AB030519); Cry2Af2 (Accession #GQ866915); Cry2Ag1 (Accession #ACH91610); Cry2Ah1 (Accession #EU939453); Cry2Ah2 (Accession #ACL80665); Cry2Ah3 (Accession #GU073380); Cry2Ah4 (Accession #KC156702); Cry2Ai1 (Accession #FJ788388); Cry2Aj (Accession #); Cry2Ak1 (Accession #KC156660); Cry2Ba1 (Accession #KC156658); Cry3Aa1 (Accession #AAA22336); Cry3Aa2 (Accession #AAA22541); Cry3Aa3 (Accession #CAA68482); Cry3Aa4 (Accession #AAA22542); Cry3Aa5 (Accession #AAA50255); Cry3Aa6 (Accession #AAC43266); Cry3Aa7 (Accession #CAB41411); Cry3Aa8 (Accession #AAS79487); Cry3Aa9 (Accession #AAW05659); Cry3Aa10 (Accession #AAU29411); Cry3Aa11 (Accession #AAW82872); Cry3Aa12 (Accession #ABY49136); Cry3Ba1 (Accession #CAA34983); Cry3Ba2 (Accession #CAA00645); Cry3Ba3 (Accession #JQ397327); Cry3Bb1 (Accession #AAA22334); Cry3Bb2 (Accession #AAA74198); Cry3Bb3 (Accession #115475); Cry3Ca1 (Accession #CAA42469); Cry4Aa1 (Accession #CAA68485); Cry4Aa2 (Accession #BAA00179); Cry4Aa3 (Accession #CAD30148); Cry4Aa4 (Accession #AFB18317); Cry4A-like (Accession #AAY96321); Cry4Ba1 (Accession #CAA30312); Cry4Ba2 (Accession #CAA30114); Cry4Ba3 (Accession #AAA22337); Cry4Ba4 (Accession #BAA00178); Cry4Ba5 (Accession #CAD30095); Cry4Ba-like (Accession #ABC47686); Cry4Ca1 (Accession #EU646202); Cry4Cb1 (Accession #FJ403208); Cry4Cb2 (Accession #FJ597622); Cry4Cc1 (Accession #FJ403207); Cry5Aa1 (Accession #AAA67694); Cry5Ab1 (Accession #AAA67693); Cry5Ac1 (Accession #134543); Cry5Ad1 (Accession #ABQ82087); Cry5Ba1 (Accession #AAA68598); Cry5Ba2 (Accession #ABW88931); Cry5Ba3 (Accession #AFJ04417); Cry5Ca1 (Accession #HM461869); Cry5Ca2 (Accession #ZP_04123426); Cry5Da1 (Accession #HM461870); Cry5Da2 (Accession #ZP_04123980); Cry5Ea1 (Accession #HM485580); Cry5Ea2 (Accession #ZP_04124038); Cry6Aa1 (Accession #AAA22357); Cry6Aa2 (Accession #AAM46849); Cry6Aa3 (Accession #ABH03377); Cry6Ba1 (Accession #AAA22358); Cry7Aa1 (Accession #AAA22351); Cry7Ab1 (Accession #AAA21120); Cry7Ab2 (Accession #AAA21121); Cry7Ab3 (Accession #ABX24522); Cry7Ab4 (Accession #EU380678); Cry7Ab5 (Accession #ABX79555); Cry7Ab6 (Accession #AC144005); Cry7Ab7 (Accession #ADB89216); Cry7Ab8 (Accession #GU145299); Cry7Ab9 (Accession #ADD92572); Cry7Ba1 (Accession #ABB70817); Cry7Bb1 (Accession #KC156653); Cry7Ca1 (Accession #ABR67863); Cry7Cb1 (Accession #KC156698); Cry7Da1 (Accession #ACQ99547); Cry7Da2 (Accession #HM572236); Cry7Da3 (Accession #KC156679); Cry7Ea1 (Accession #HM035086); Cry7Ea2 (Accession #HM132124); Cry7Ea3 (Accession #EEM19403); Cry7Fa1 (Accession #HM035088); Cry7Fa2 (Accession #EEM19090); Cry7Fb1 (Accession #HM572235); Cry7Fb2 (Accession #KC156682); Cry7Ga1 (Accession #HM572237); Cry7Ga2 (Accession #KC156669); Cry7Gb1 (Accession #KC156650); Cry7Gc1 (Accession #KC156654); Cry7Gd1 (Accession #KC156697); Cry7Ha1 (Accession #KC156651); Cry7Ia1 (Accession #KC156665); Cry7Ja1 (Accession

KC156671); Cry7Ka1 (Accession #KC156680); Cry7Kb1 (Accession #BAM99306); Cry7La1 (Accession #BAM99307); Cry8Aa1 (Accession #AAA21117); Cry8Ab1 (Accession #EU044830); Cry8Ac1 (Accession #KC156662); Cry8Ad1 (Accession #KC156684); Cry8Ba1 (Accession #AAA21118); Cry8Bb1 (Accession #CAD57542); Cry8Bc1 (Accession #CAD57543); Cry8Ca1 (Accession #AAA21119); Cry8Ca2 (Accession #AAR98783); Cry8Ca3 (Accession #EU625349); Cry8Ca4 (Accession #ADB54826); Cry8Da1 (Accession #BAC07226); Cry8Da2 (Accession #BD133574); Cry8Da3 (Accession #BD133575); Cry8db1 (Accession #BAF93483); Cry8Ea1 (Accession #AAQ73470); Cry8Ea2 (Accession #EU047597); Cry8Ea3 (Accession #KC855216); Cry8Fa1 (Accession #AAT48690); Cry8Fa2 (Accession #HQ174208); Cry8Fa3 (Accession #AFH78109); Cry8Ga1 (Accession #AAT46073); Cry8Ga2 (Accession #ABC42043); Cry8Ga3 (Accession #FJ198072); Cry8Ha1 (Accession #AAW81032); Cry8Ia1 (Accession #EU381044); Cry8Ia2 (Accession #GU073381); Cry8Ia3 (Accession #HM044664); Cry8Ia4 (Accession #KC156674); Cry8Ib1 (Accession #GU325772); Cry8Ib2 (Accession #KC156677); Cry8Ja1 (Accession #EU625348); Cry8Ka1 (Accession #FJ422558); Cry8Ka2 (Accession #ACN87262); Cry8Kb1 (Accession #HM123758); Cry8Kb2 (Accession #KC156675); Cry8La1 (Accession #GU325771); Cry8Ma1 (Accession #HM044665); Cry8Ma2 (Accession #EEM86551); Cry8Ma3 (Accession #HM210574); Cry8Na1 (Accession #HM640939); Cry8Pa1 (Accession #HQ388415); Cry8Qa1 (Accession #HQ441166); Cry8Qa2 (Accession #KC152468); Cry8Ra1 (Accession #AFP87548); Cry8Sa1 (Accession #JQ740599); Cry8Ta1 (Accession #KC156673); Cry8-like (Accession #FJ770571); Cry8-like (Accession #ABS53003); Cry9Aa1 (Accession #CAA41122); Cry9Aa2 (Accession #CAA41425); Cry9Aa3 (Accession #GQ249293); Cry9Aa4 (Accession #GQ249294); Cry9Aa5 (Accession #JX174110); Cry9Aa like (Accession #AAQ52376); Cry9Ba1 (Accession #CAA52927); Cry9Ba2 (Accession #GU299522); Cry9Bb1 (Accession #AAV28716); Cry9Ca1 (Accession #CAA85764); Cry9Ca2 (Accession #AAQ52375); Cry9Da1 (Accession #BAA19948); Cry9Da2 (Accession #AAB97923); Cry9Da3 (Accession #GQ249293); Cry9Da4 (Accession #GQ249297); Cry9db1 (Accession #AAX78439); Cry9Dc1 (Accession #KC156683); Cry9Ea1 (Accession #BAA34908); Cry9Ea2 (Accession #AAO12908); Cry9Ea3 (Accession #ABM21765); Cry9Ea4 (Accession #ACE88267); Cry9Ea5 (Accession #ACF04743); Cry9Ea6 (Accession #ACG63872); Cry9Ea7 (Accession #FJ380927); Cry9Ea8 (Accession #GQ249292); Cry9Ea9 (Accession #JN651495); Cry9Eb1 (Accession #CAC50780); Cry9Eb2 (Accession #GQ249298); Cry9Eb3 (Accession #KC156646); Cry9Ec1 (Accession #AAC63366); Cry9Ed1 (Accession #AAX78440); Cry9Ee1 (Accession #GQ249296); Cry9Ee2 (Accession #KC156664); Cry9Fa1 (Accession #KC156692); Cry9Ga1 (Accession #KC156699); Cry9-like (Accession #AAC63366); Cry10Aa1 (Accession #AAA22614); Cry10Aa2 (Accession #E00614); Cry10Aa3 (Accession #CAD30098); Cry10Aa4 (Accession #AFB18318); Cry10A-like (Accession #DQ167578); Cry11Aa1 (Accession #AAA22352); Cry11Aa2 (Accession #AAA22611); Cry11Aa3 (Accession #CAD30081); Cry11Aa4 (Accession #AFB18319); Cry11Aa-like (Accession #DQ166531); Cry11Ba1 (Accession #CAA60504); Cry11Bb1 (Accession #AAC97162); Cry11Bb2 (Accession #HM068615); Cry12Aa1 (Accession #AAA22355); Cry13Aa1 (Accession #AAA22356); Cry14Aa1 (Accession #AAA21516); Cry14Ab1 (Accession #KC156652); Cry15Aa1 (Accession #AAA22333); Cry16Aa1 (Accession #CAA63860); Cry17Aa1 (Accession #CAA67841); Cry18Aa1 (Accession #CAA67506); Cry18Ba1 (Accession #AAF89667); Cry18Ca1 (Accession #AAF89668); Cry19Aa1 (Accession #CAA68875); Cry19Ba1 (Accession #BAA32397); Cry19Ca1 (Accession #AFM37572); Cry20Aa1 (Accession #AAB93476); Cry20Ba1 (Accession #ACS93601); Cry20Ba2 (Accession #KC156694); Cry20-like (Accession #GQ144333); Cry21Aa1 (Accession #132932); Cry21Aa2 (Accession #166477); Cry21Ba1 (Accession #BAC06484); Cry21Ca1 (Accession #JF521577); Cry21Ca2 (Accession #KC156687); Cry21Da1 (Accession #JF521578); Cry22Aa1 (Accession #134547); Cry22Aa2 (Accession #CAD43579); Cry22Aa3 (Accession #ACD93211); Cry22Ab1 (Accession #AAK50456); Cry22Ab2 (Accession #CAD43577); Cry22Ba1 (Accession #CAD43578); Cry22Bb1 (Accession #KC156672); Cry23Aa1 (Accession #AAF76375); Cry24Aa1 (Accession #AAC61891); Cry24Ba1 (Accession #BAD32657); Cry24Ca1 (Accession #CAJ43600); Cry25Aa1 (Accession #AAC61892); Cry26Aa1 (Accession #AAD25075); Cry27Aa1 (Accession #BAA82796); Cry28Aa1 (Accession #AAD24189); Cry28Aa2 (Accession #AAG00235); Cry29Aa1 (Accession #CAC80985); Cry30Aa1 (Accession #CAC80986); Cry30Ba1 (Accession #BAD00052); Cry30Ca1 (Accession #BAD67157); Cry30Ca2 (Accession #ACU24781); Cry30Da1 (Accession #EF095955); Cry30db1 (Accession #BAE80088); Cry30Ea1 (Accession #ACC95445); Cry30Ea2 (Accession #FJ499389); Cry30Fa1 (Accession #AC122625); Cry30Ga1 (Accession #ACG60020); Cry30Ga2 (Accession #HQ638217); Cry31Aa1 (Accession #BAB11757); Cry31Aa2 (Accession #AAL87458); Cry31Aa3 (Accession #BAE79808); Cry31Aa4 (Accession #BAF32571); Cry31Aa5 (Accession #BAF32572); Cry31Aa6 (Accession #BAI44026); Cry31Ab1 (Accession #BAE79809); Cry31Ab2 (Accession #BAF32570); Cry31Ac1 (Accession #BAF34368); Cry31Ac2 (Accession #AB731600); Cry31Ad1 (Accession #BAI44022); Cry32Aa1 (Accession #AAG36711); Cry32Aa2 (Accession #GU063849); Cry32Ab1 (Accession #GU063850); Cry32Ba1 (Accession #BAB78601); Cry32Ca1 (Accession #BAB78602); Cry32Cb1 (Accession #KC156708); Cry32Da1 (Accession #BAB78603); Cry32Ea1 (Accession #GU324274); Cry32Ea2 (Accession #KC156686); Cry32Eb1 (Accession #KC156663); Cry32Fa1 (Accession #KC156656); Cry32Ga1 (Accession #KC156657); Cry32Ha1 (Accession #KC156667); Cry32Hb1 (Accession #KC156666); Cry32Ia1 (Accession #KC156667); Cry32Ja1 (Accession #KC156685); Cry32Ka1 (Accession #KC156688); Cry32La1 (Accession #KC156689); Cry32Ma1 (Accession #KC156690); Cry32Mb1 (Accession #KC156704); Cry32Na1 (Accession #KC156691); Cry32Oa1 (Accession #KC156703); Cry32Pa1 (Accession #KC156705); Cry32Qa1 (Accession #KC156706); Cry32Ra1 (Accession #KC156707); Cry32Sa1 (Accession #KC156709); Cry32Ta1 (Accession #KC156710); Cry32Ua1 (Accession #KC156655); Cry33Aa1 (Accession #AAL26871); Cry34Aa1 (Accession #AAG50341); Cry34Aa2 (Accession #AAK64560); Cry34Aa3 (Accession #AAT29032); Cry34Aa4 (Accession #AAT29030); Cry34Ab1 (Accession #AAG41671); Cry34Ac1 (Accession #AAG50118); Cry34Ac2 (Accession #AAK64562); Cry34Ac3 (Accession #AAT29029); Cry34Ba1 (Accession #AAK64565); Cry34Ba2 (Accession #AAT29033);

Cry34Ba3 (Accession #AAT29031); Cry35Aa1 (Accession #AAG50342); Cry35Aa2 (Accession #AAK64561); Cry35Aa3 (Accession #AAT29028); Cry35Aa4 (Accession #AAT29025); Cry35Ab1 (Accession #AAG41672); Cry35Ab2 (Accession #AAK64563); Cry35Ab3 (Accession #AY536891); Cry35Ac1 (Accession #AAG50117); Cry35Ba1 (Accession #AAK64566); Cry35Ba2 (Accession #AAT29027); Cry35Ba3 (Accession #AAT29026); Cry36Aa1 (Accession #AAK64558); Cry37Aa1 (Accession #AAF76376); Cry38Aa1 (Accession #AAK64559); Cry39Aa1 (Accession #BAB72016); Cry40Aa1 (Accession #BAB72018); Cry40Ba1 (Accession #BAC77648); Cry40Ca1 (Accession #EU381045); Cry40Da1 (Accession #ACF15199); Cry41Aa1 (Accession #BAD35157); Cry41Ab1 (Accession #BAD35163); Cry41Ba1 (Accession #HM461871); Cry41Ba2 (Accession #ZP_04099652); Cry42Aa1 (Accession #BAD35166); Cry43Aa1 (Accession #BAD15301); Cry43Aa2 (Accession #BAD95474); Cry43Ba1 (Accession #BAD15303); Cry43Ca1 (Accession #KC156676); Cry43Cb1 (Accession #KC156695); Cry43Cc1 (Accession #KC156696); Cry43-like (Accession #BAD15305); Cry44Aa (Accession #BAD08532); Cry45Aa (Accession #BAD22577); Cry46Aa (Accession #BAC79010); Cry46Aa2 (Accession #BAG68906); Cry46Ab (Accession #BAD35170); Cry47Aa (Accession #AAY24695); Cry48Aa (Accession #CAJ18351); Cry48Aa2 (Accession #CAJ86545); Cry48Aa3 (Accession #CAJ86546); Cry48Ab (Accession #CAJ86548); Cry48Ab2 (Accession #CAJ86549); Cry49Aa (Accession #CAH56541); Cry49Aa2 (Accession #CAJ86541); Cry49Aa3 (Accession #CAJ86543); Cry49Aa4 (Accession #CAJ86544); Cry49Ab1 (Accession #CAJ86542); Cry50Aa1 (Accession #BAE86999); Cry50Ba1 (Accession #GU446675); Cry50Ba2 (Accession #GU446676); Cry51Aa1 (Accession #ABI14444); Cry51Aa2 (Accession #GU570697); Cry52Aa1 (Accession #EF613489); Cry52Ba1 (Accession #FJ361760); Cry53Aa1 (Accession #EF633476); Cry53Ab1 (Accession #FJ361759); Cry54Aa1 (Accession #ACA52194); Cry54Aa2 (Accession #GQ140349); Cry54Ba1 (Accession #GU446677); Cry55Aa1 (Accession #ABW88932); Cry54Ab1 (Accession #JQ916908); Cry55Aa2 (Accession #AAE33526); Cry56Aa1 (Accession #ACU57499); Cry56Aa2 (Accession #GQ483512); Cry56Aa3 (Accession #JX025567); Cry57Aa1 (Accession #ANC87261); Cry58Aa1 (Accession #ANC87260); Cry59Ba1 (Accession #JN790647); Cry59Aa1 (Accession #ACR43758); Cry60Aa1 (Accession #ACU24782); Cry60Aa2 (Accession #EA057254); Cry60Aa3 (Accession #EEM99278); Cry60Ba1 (Accession #GU810818); Cry60Ba2 (Accession #EA057253); Cry60Ba3 (Accession #EEM99279); Cry61Aa1 (Accession #HM035087); Cry61Aa2 (Accession #HM132125); Cry61Aa3 (Accession #EEM19308); Cry62Aa1 (Accession #HM054509); Cry63Aa1 (Accession #BAI44028); Cry64Aa1 (Accession #BAJ05397); Cry65Aa1 (Accession #HM461868); Cry65Aa2 (Accession #ZP_04123838); Cry66Aa1 (Accession #HM485581); Cry66Aa2 (Accession #ZP_04099945); Cry67Aa1 (Accession #HM485582); Cry67Aa2 (Accession #ZP_04148882); Cry68Aa1 (Accession #HQ113114); Cry69Aa1 (Accession #HQ401006); Cry69Aa2 (Accession #JQ821388); Cry69Ab1 (Accession #JN209957); Cry70Aa1 (Accession #JN646781); Cry70Ba1 (Accession #AD051070); Cry70Bb1 (Accession #EEL67276); Cry71Aa1 (Accession #JX025568); Cry72Aa1 (Accession #JX025569); CytIAa (GenBank Accession Number X03182); CytIAb (GenBank Accession Number X98793); Cyt1 B (GenBank Accession Number U37196); Cyt2A (GenBank Accession Number Z14147); and Cyt2B (GenBank Accession Number U52043).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of cry proteins such as Cry1A, Cry3A) of U.S. Pat. Nos. 8,304,604, 8,304,605 and 8,476,226; Cry1B of U.S. patent application Ser. No. 10/525,318; Cry1C of U.S. Pat. No. 6,033,874; Cry1F of U.S. Pat. Nos. 5,188,960 and 6,218,188; Cry1A/F chimeras of U.S. Pat. Nos. 7,070,982; 6,962,705 and 6,713,063; a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as members of the Cry9A, Cry9B, Cry9C, Cry9D, Cry9E and Cry9F families; a Cry15 protein of Naimov, et al., (2008) *Applied and Environmental Microbiology*, 74:7145-7151; a Cry22, a Cry34Ab1 protein of U.S. Pat. Nos. 6,127,180, 6,624,145 and 6,340,593; a CryET33 and cryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry51 protein, a Cry binary toxin; a TIC901 or related toxin; TIC807 of US Patent Application Publication Number 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020 and AXMI-021 of WO 2006/083891; AXMI-010 of WO 2005/038032; AXMI-003 of WO 2005/021585; AXMI-008 of US Patent Application Publication Number 2004/0250311; AXMI-006 of US Patent Application Publication Number 2004/0216186; AXMI-007 of US Patent Application Publication Number 2004/0210965; AXMI-009 of US Patent Application Number 2004/0210964; AXMI-014 of US Patent Application Publication Number 2004/0197917; AXMI-004 of US Patent Application Publication Number 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US Patent Application Publication Number 2011/0023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063 and AXMI-064 of US Patent Application Publication Number 2011/0263488; AXMI-R1 and related proteins of US Patent Application Publication Number 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230 and AXMI231 of WO 2011/103247; AXMI-115, AXMI-113, AXMI-005, AXMI-163 and AXMI-184 of U.S. Pat. No. 8,334,431; AXMI-001, AXMI-002, AXMI-030, AXMI-035 and AXMI-045 of US Patent Application Publication Number 2010/0298211; AXMI-066 and AXMI-076 of US Patent Application Publication Number 2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US Patent Application Publication Number 2010/0005543, AXMI232, AXMI233 and AXMI249 of US Patent Application Publication Number 201400962281; cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to plants expressing Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, Cry9c and CBI-Bt have received regulatory approval (see, Sanahuja, (2011) *Plant Biotech Journal* 9:283-300 and the CERA. (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1 Fa (US2012/0317682); Cry1 BE & Cry1F (US2012/0311746); Cry1 CA & Cry1AB (US2012/0311745); Cry1F & CryCa (US2012/0317681); Cry1DA & Cry1BE (US2012/0331590); Cry1DA & Cry1Fa (US2012/0331589); Cry1AB & Cry1BE (US2012/0324606); Cry1Fa & Cry2Aa and Cry1I & Cry1 E (US2012/0324605); Cry34Ab/35Ab and Cry6Aa (US20130167269); Cry34Ab/VCry35Ab & Cry3Aa (US20130167268); and Cry3A and Cry1Ab or Vip3Aa (US20130116170). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279 6,137,033, 7,244,820, 7,615,686, and 8,237,020 and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

The examples below describe some representative protocols and techniques for simulating plant insect feeding conditions and/or evaluating plants under such conditions.

1. Progeny of a transformed plant which is hemizygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct (i.e., the progeny not comprising the recombinant DNA construct is the control or reference plant).

2. Introgression of a recombinant DNA construct into an inbred line, such as in maize, or into a variety, such as in soybean: the introgressed line would typically be measured relative to the parent inbred or variety line (i.e., the parent inbred or variety line is the control or reference plant).

3. Two hybrid lines, wherein the first hybrid line is produced from two parent inbred lines, and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A plant comprising a recombinant DNA construct: the plant may be assessed or measured relative to a control plant not comprising the recombinant DNA construct but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct).

Furthermore, one of ordinary skill in the art would readily recognize that a suitable control or reference plant to be utilized when assessing or measuring an agronomic characteristic or phenotype of a transgenic plant would not include a plant that had been previously selected, via mutagenesis or transformation, for the desired agronomic characteristic or phenotype.

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Lepidoptera and Coleoptera.

Those skilled in the art will recognize that not all compounds are equally effective against all pests. Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae including *Spodoptera frugiperda* JE Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A.* orthogonia Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); Egira (Xylomyges) curialis Grote (citrus cutworm); *Mythimna* separate (Oriental Armyworm); borers, casebearers, webworms, coneworms, grass moths from the family Crambidae including *Ostrinia furnacalis* (Asian Corn Borer) and *Ostrinia nubilalis* (European Corn Borer), and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); Corcyra cephalonica Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit *tortrix* moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermüller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); Datana integerrima Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Méneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenée (omnivorous looper); Schizura concinna J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenée; *Malacosoma* spp. and *Orgyia* spp.

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape *colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Géhin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; *Cicadella viridis* (Linnaeus) from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, *phylloxera* from the family Phylloxeridae, mealybugs from the family Pseudococcidae, scales from the families Asterolecanidae, Coccidae, Dactylopiidae, Diaspididae, Eriococcidae, Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cincticeps* Uhler (green leafhopper); *N. nigropictus* Stål (rice leafhopper); *Nilaparvata lugens* Stål (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); Magicicada *septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear *psylla*); *Trioza diospyri* Ashmead (persimmon *psylla*).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schsffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, Calocoris *norvegicus* Gmelin (strawberry bug); Orthops *campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families' Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Dichelops furcatus, Dichelops melacanthus*, and *Bagrada hilaris* (Bagrada Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Methods for measuring pesticidal activity are well known in the art. See, for example, Czapla and Lang, (1990) *J. Econ. Entomol.* 83: 2480-2485; Andrews, et al., (1988) *Biochem. J.* 252:199-206; Marrone, et al., (1985) *J. of Economic Entomology* 78:290-293 and U.S. Pat. No. 5,743, 477, all of which are herein incorporated by reference in their entirety. Generally, the protein is mixed and used in feeding assays. See, for example Marrone, et al., (1985) J. of Economic Entomology 78:290-293. Such assays can include contacting plants with one or more pests and determining the plant's ability to survive and/or cause the death of the pests.

As used herein, the term "pesticidal activity" is used to refer to activity of an organism or a substance (such as, for example, a protein), whether toxic or inhibitory, that can be measured by, but is not limited to, pest mortality, pest weight loss, pest repellency, pest growth stunting, and other behavioral and physical changes of a pest after feeding and exposure for an appropriate length of time. In this manner, pesticidal activity impacts at least one measurable parameter of pest fitness. Similarly, "insecticidal activity" may be used to refer to "pesticidal activity" when the pest is an insect pest. "Stunting" is intended to mean greater than 50% inhibition of growth as determined by weight. General procedures for monitoring insecticidal activity include addition of the experimental compound or organism to the diet source in an enclosed container. Assays for assessing insecticidal activity are well known in the art. See, e.g., U.S. Pat. Nos. 6,570,005 and 6,339,144; herein incorporated by reference in their entirety. The optimal developmental stage for testing for insecticidal activity is larvae or immature forms of an insect of interest. The insects may be reared in total darkness at about 20~30° C. and about 30%~70% relative humidity. Bioassays may be performed as described in Czapla and Lang (1990) J. Econ. Entomol. 83(6):2480-2485. Methods of rearing insect larvae and performing bioassays are well known to one of ordinary skill in the art.

Toxic and inhibitory effects of insecticidal proteins include, but are not limited to, stunting of larval growth, killing eggs or larvae, reducing either adult or juvenile feeding on transgenic plants relative to that observed on wild-type, and inducing avoidance behavior in an insect as it relates to feeding, nesting, or breeding as described herein, insect resistance can be conferred to an organism by introducing a nucleotide sequence encoding an insecticidal protein or applying an insecticidal substance, which includes, but is not limited to, an insecticidal protein, to an organism (e.g., a plant or plant part thereof). As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

Methods

Methods include but are not limited to methods for increasing tolerance in a plant to an insect pest, methods for evaluating insect resistance, methods for controlling an insect population, methods for killing an insect population, methods for controlling an insect population resistance to an insecticidal polypeptide, and methods for producing seed.

Methods include but are not limited to the following:

A method for transforming a cell comprising transforming a cell with any of the isolated polynucleotides of the present disclosure. The cell transformed by this method is also included. In particular embodiments, the cell is eukaryotic cell, e.g., a yeast, insect or plant cell, or prokaryotic, e.g., a bacterium.

A method for producing a transgenic plant comprising transforming a plant cell with any of the isolated polynucleotides or recombinant DNA constructs of the present disclosure and regenerating a transgenic plant from the transformed plant cell. The disclosure is also directed to the transgenic plant produced by this method, and transgenic seed obtained from this transgenic plant.

A method for isolating a polypeptide of the disclosure from a cell or culture medium of the cell, wherein the cell comprises a recombinant DNA construct comprising a polynucleotide of the disclosure operably linked to at least one regulatory element, and wherein the transformed host cell is grown under conditions that are suitable for expression of the recombinant DNA construct.

A method of altering the level of expression of a polypeptide of the disclosure in a host cell comprising: (a) transforming a host cell with a recombinant DNA construct of the present disclosure; and (b) growing the transformed host cell under conditions that are suitable for expression of the recombinant DNA construct wherein expression of the recombinant DNA construct results in production of altered levels of the polypeptide of the disclosure in the transformed host cell.

A method of increasing tolerance in a plant to an insect pest comprising: (a) introducing into a regenerable plant cell a recombinant DNA construct comprising a polynucleotide operably linked to at least one regulatory element (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, when compared to SEQ ID NO: 6, 9 or 12; and (b) regenerating a transgenic plant from the regenerable plant cell after step (a), wherein the transgenic plant comprises in its genome the recombinant DNA construct and exhibits increased tolerance to an insect pest when compared to a control plant not comprising the recombinant DNA construct. The method may further comprise (c) obtaining a progeny plant derived from the transgenic plant, wherein the progeny plant comprises in its genome the recombinant DNA construct and exhibits increased tolerance to an insect pest when compared to a control plant not comprising the recombinant DNA construct.

A method of increasing tolerance in a plant to an insect pest, comprising: (a) introducing into a regenerable plant cell a DNA construct comprising at least one heterologous regulatory element operably linked to a nucleic acid sequence encoding a SLT1, DN-ITP6 or DN-ITP7 polypeptide in the plant genome; and (b) regenerating a transgenic plant from the regenerable plant cell after step (a), wherein the transgenic plant comprises in its genome the DNA construct, has increased expression of the SLT1, DN-ITP6 or DN-ITP7 polypeptide, and exhibits increased tolerance to an insect pest when compared to a control plant not comprising the DNA construct. The method may further comprise (c) obtaining a progeny plant derived from the transgenic plant, wherein the progeny plant comprises in its genome the DNA construct, has increased expression of the SLT1, DN-ITP6 or DN-ITP7 polypeptide and exhibits increased tolerance to an insect pest compared to a control plant not comprising the DNA construct.

In some embodiments, methods are provided for controlling an insect pest comprising over-expressing in a plant a SLT1, DN-ITP6 or DN-ITP7 polypeptide. In some embodiments, the method for controlling an insect pest comprises transforming a plant or plant cell with the DNA constructs of the present disclosure.

In some embodiments, methods are provided for killing an insect pest comprising over-expressing in a plant a SLT1, DN-ITP6 or DN-ITP7 polypeptide. In some embodiments, the method for killing an insect pest comprises transforming a plant or plant cell with the DNA constructs of the present disclosure.

A method of evaluating tolerance to an insect pest in a plant, comprising (a) introducing into a regenerable plant cell a recombinant DNA construct comprising a polynucleotide operably linked to at least one regulatory element (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity when compared to SEQ ID NO: 6, 9 or 12; (b) regenerating a transgenic plant from the regenerable plant cell after step (a), wherein the transgenic plant comprises in its genome the recombinant DNA construct; and (c) evaluating the transgenic plant for insect tolerance compared to a control plant not comprising the recombinant DNA construct. The method may further comprise (d) obtaining a progeny plant derived from the transgenic plant, wherein the progeny plant comprises in its genome the recombinant DNA construct; and (e) evaluating the progeny plant for insect tolerance compared to a control plant not comprising the recombinant DNA construct.

A method of producing seed comprising any of the preceding methods, and further comprising obtaining seeds from the progeny plant, wherein the seeds comprise in their genome the recombinant DNA construct.

In some embodiments the disclosure provides seeds that comprise in their genome the recombinant DNA construct of the disclosure.

Seed Treatment

To protect and to enhance yield production and trait technologies, seed treatment options can provide additional crop plan flexibility and cost effective control against insects, weeds and diseases. Seed material can be treated with one or more of the insecticidal proteins or polypeptides disclosed herein. For e.g., such seed treatments can be applied on seeds that contain a transgenic trait including transgenic corn, soy, *brassica*, cotton or rice.

Combinations of one or more of the insecticidal proteins or polypeptides disclosed herein and other conventional seed treatments are contemplated. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., and Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis* species), *bradyrhizobium* spp. (including one or more of *betae, canar-*

*iense, elkanii, iriomotense, japonicum,* liaonigense, *pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium,* penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma,* trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring tolerance to an insect pest may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

In any of the preceding methods or any other embodiments of methods of the present disclosure, the step of determining an alteration of an agronomic characteristic in a transgenic plant, if applicable, may comprise determining whether the transgenic plant exhibits an alteration of at least one agronomic characteristic when compared, under varying environmental conditions, to a control plant not comprising the recombinant DNA construct.

In any of the preceding methods or any other embodiments of methods of the present disclosure, the step of determining an alteration of an agronomic characteristic in a progeny plant, if applicable, may comprise determining whether the progeny plant exhibits an alteration of at least one agronomic characteristic when compared, under varying environmental conditions, to a control plant not comprising the recombinant DNA construct.

In any of the preceding methods or any other embodiments of methods of the present disclosure, in the introducing step the regenerable plant cell may comprises a callus cell, an embryogenic callus cell, a gametic cell, a meristematic cell, or a cell of an immature embryo. The regenerable plant cells may derive from an inbred maize plant.

In any of the preceding methods or any other embodiments of methods of the present disclosure, the regenerating step may comprise: (i) culturing the transformed plant cells in a media comprising an embryogenic promoting hormone until callus organization is observed; (ii) transferring the transformed plant cells of step (i) to a first media which includes a tissue organization promoting hormone; and (iii) sub-culturing the transformed plant cells after step (ii) onto a second media, to allow for shoot elongation, root development or both.

In any of the preceding methods or any other embodiments of methods of the present disclosure, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant disclosure.

The introduction of recombinant DNA constructs of the present disclosure into plants may be carried out by any suitable technique, including but not limited to direct DNA uptake, chemical treatment, electroporation, microinjection, cell fusion, infection, vector mediated DNA transfer, bombardment, or *Agrobacterium* mediated transformation. Techniques for plant transformation and regeneration have been described in International Patent Publication WO 2009/006276, the contents of which are herein incorporated by reference.

In addition, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" engineered endonucleases such as meganucleases produced to modify plant genomes (e.g., WO 2009/114321; Gao et al. (2010) Plant Journal 1:176-187). Another site-directed engineering is through the use of zinc finger domain recognition coupled with the restriction properties of restriction enzyme (e.g., Urnov, et al. (2010) *Nat Rev Genet.* 11(9):636-46; Shukla, et al. (2009) *Nature* 459 (7245):437-41). A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326 (5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The CRISPR/Cas system allows targeted cleavage of genomic DNA guided by a customizable small noncoding RNA.

The development or regeneration of plants containing the foreign, exogenous isolated nucleic acid fragment that encodes a protein of interest is well known in the art. The regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

Stacking of Traits in Transgenic Plant

Transgenic plants may comprise a stack of one or more insecticidal or insect tolerance polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and cotransformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

EXAMPLES

Example 1

Creation of a Rice Population with an Activation-Tagging Construct

A binary construct that contains four multimerized enhancers elements derived from the Cauliflower Mosaic Virus 35S (CaMV 35S) promoter was used, and the rice activation tagging population was developed from Zhonghua 11 (*Oryza sativa* L.) which was transformed by Agrobacteria-mediated transformation method as described by Lin and Zhang ((2005) *Plant Cell Rep.* 23: 540-547). Zhonghua 11 was cultivated by the Institute of Crop Sciences, Chinese Academy of Agricultural Sciences. The first batch of seeds used in this research was provided by Beijing Weiming Kaituo Agriculture Biotech Co., Ltd. Calli induced from embryos was transformed with Agrobacteria with the construct. The transgenic lines generated were developed and the transgenic seeds were harvested to form the rice activation tagging population.

Example 2

Seedling Screen to Identify Lines with Enhanced Tolerance to Insects Under Laboratory Conditions Asian corn borer (ACB) (*Ostrinia furnacalis* (Guenée)) is an important insect pest of maize in Asia. This insect is distributed from China to Australia and the Solomon Islands. In northern parts of its range, the moths have one or a few generations per year, but in the tropics, generations are continuous and overlapping. The caterpillars can cause severe yield losses in corn, both by damage to the kernels and by feeding on the tassels, leaves, and stalks. Survival and growth of the caterpillar is highest on the reproductive parts of the plant. Other economic plants attacked include bell pepper, ginger and sorghum. Recently, the Asian corn borer appears to have become an important pest of cotton. A number of wild grasses are also used as hosts (D. M. Nafusa & I. H. Schreinera. 2012. Review of the biology and control of the Asian corn borer, *Ostrinia furnacalis* (Lep: Pyralidae). *Tropical Pest Management.* 37: 41-56).

ACB insect was used to identify rice ATLs which can inhibit larva development. Asian corn borer populations were obtained from the Institute of Plant Protection of Chinese Academy of Agricultural Sciences. This population was reared for more than 10 generations at 25-27° C., 60-80% relative humidity, under photo-period of 16L: 8D. The larvae were fed with artificial diet (Zhou Darong, Ye Zhihua, Wang Zhenying, 1995), and the eggs were hatched in incubator at 27° C. The newly hatched larvae were used in assays.

The T2 seeds which showed red color under green fluorescent light (transgenic seeds) were used for insect tolerance assays except as otherwise specifically noted. One hundred fifty seeds of each activation tagged line (ATL) were sterilized by 800 ppm carbendazol for 8 h at 32° C. and washed 3-5 times, then placed on a layer of wet gauze in petri dish (12×12 cm). The germinated seeds were cultured in distilled water at 28° C. for 10 days and the seedlings which were 8-10 cm in height were used to feed ACB larvae.

Screening Method:

The 32-well plates (4×4×2 cm for each well) (Pitman, N.J. USA-609-582-2392) were used and one-third volume of 1% agar solution was filled in each well to keep humidity. The 32-well plate could be divided into 8 blocks with each block of 4 wells for one rice ATL seedlings. Twenty rice seedlings without seeds and roots were inserted into the agar, six ACB neonate larvae were inoculated into the well with a brush, and the wells were covered with lids (Pitman, N.J. USA-609-582-2392). The tissue cultured ZH11 (ZH11-TC) were used as control, and the control seedlings were randomly placed in the blocks. The plates were placed in a chamber with temperature 27.5° C. and 60% relative humidity, and rotated 90 degree each day from the second day. The insect larval development was measured visually 5 days later, and the tolerant values were calculated.

The three largest larvae in each well were selected, compared with the larvae in the well with ZH11-TC seedlings, and then a tolerant value was obtained according to Table 2. If the larva in the control well developed to third instar, then the larval development was considered as normal and the tolerant value is 0; if the larva developed to second instar, it was smaller compared to the normal developed larva and the tolerant value is 1; and if the larva developed to first instar, it is very smaller and the tolerant value is 2.

Larva growth inhibitory rate was used as a parameter for ACB insect tolerance assay, which is the percentage of the inhibited number over the statistics number of larva, wherein the inhibited number of larva is the sum of the tolerant value of 12 test insects from four wells in one repeat and the statistics number of larva is the sum of the number of all the observed insects and number of larva at $1^{st}$ instar. Then the raw data was analyzed by Chi-square, the lines with P<0.01 were considered as ACB tolerance positive lines.

TABLE 2

Scoring Scales for Asian corn borer

| Tolerant value | Instars of larva | Size of larva |
| --- | --- | --- |
| 0 | $3^{rd}$ instar | Normal |
| 1 | $2^{nd}$ instar | Smaller |
| 2 | $1^{st}$ instar | Severe smaller |

The ACB tolerant lines from the primary screens were re-screened in two continued screens ($2^{nd}$ and $3^{rd}$ round of screens) with two repeats to confirm the insect tolerance. The ATLs which passed the $3^{rd}$ screens were considered as ACB tolerant lines.

Screening Results:

1) AH43610 Seedlings

After ACB neonate larvae inoculating seedlings for 5 days in the screens, the seedlings of ZH11-TC were significantly damaged by ACB insects, while AH43610 seedling were less damaged, and the insects fed with AH43610 was smaller than that fed with ZH11-TC control. As shown in Table 3, ten of the 12 observed larvae with AH43610 seedlings developed to $2^{nd}$ instar, whereas 11 of the 12 observed insects with ZH11-TC seedlings grew normally to $3^{rd}$ instar. The larvae growth inhibitory rate of AH43610 was 83.33%, which was significantly greater than that of ZH11-TC seedlings (8.33%). These results show that AH43610 seedlings inhibited the development of ACB larvae. In the second screen, the larvae growth inhibitory rates of AH43610 in two repeats were 41.67% and 66.67%, respectively, whereas the larvae growth inhibitory rates of ZH11-TC controls both were 0.00%. The larvae growth inhibitory rates of AH43610 were significantly greater than ZH11-TC. One repeat of AH43610 in the $3^{rd}$ screening displayed the same trend, and in the other repeat, AH43610 exhibited greater larvae growth inhibitory rate. These results consistently demonstrate that feeding ACB with AH43610 seedlings can prevent the ACB larvae from developing to adults.

TABLE 3

Asian corn borer assay of AH43610 seedlings under laboratory screening condition

| Line ID | Screening round | Number of larvae at $1^{st}$ instar | Number of larvae at $2^{nd}$ instar | Number of total observed larvae | Larvae growth inhibitory rate (%) | P value | P ≤ 0.01 |
| --- | --- | --- | --- | --- | --- | --- | --- |
| ZH11-TC | 1-1 | 0 | 1 | 12 | 8.33 | | |
| AH43610 | | 0 | 10 | 12 | 83.33 | 0.0002 | Y |
| ZH11-TC | 2-1 | 0 | 0 | 12 | 0.00 | | |
| AH43610 | | 0 | 5 | 12 | 41.67 | 0.0120 | |
| ZH11-TC | 2-2 | 0 | 0 | 12 | 0.00 | | |
| AH43610 | | 0 | 6 | 9 | 66.67 | 0.0008 | Y |
| ZH11-TC | 3-1 | 0 | 0 | 22 | 0.00 | | |
| AH43610 | | 0 | 5 | 18 | 27.78 | 0.0082 | Y |
| ZH11-TC | 3-2 | 0 | 6 | 24 | 25.00 | | |
| AH43610 | | 0 | 6 | 21 | 28.57 | 0.7869 | |

2) AH35009 Seedlings

After ACB neonate larvae inoculating seedlings for 5 days in the screens, the seedlings of ZH11-TC were significantly damaged by ACB insects, while AH35009 seedling were less damaged, and the insects fed with AH35009 was smaller than that fed with ZH11-TC control. Table 4 shows the three rounds screening results for AH35009 seedlings. In the first screening, all six insects in AH35009 seedlings' wells developed to $2^{nd}$ instar, while all observed 12 insects fed with ZH11-TC seedlings normally grew to $3^{rd}$ instar. The larva growth inhibitory rate of AH35009 (100%) was significantly greater than that of ZH11-TC seedlings (0.00%). These results indicated that AH35009 seedlings inhibited the development of ACB larva. Therefore, it was further screened. In the second screening, the larva growth inhibitory rates of AH35009 in two repeats were 91% and 50%, respectively, which were significantly greater than that of their corresponding ZH11-TC controls. The larva growth inhibitory rates of AH35009 seedlings were also significantly greater than that of their corresponding ZH11-TC controls in one repeat of $3^{rd}$ round screening. These results clearly and consistently demonstrate that AH35009 seedling can inhibit the development of ACB insect and AH35009 was an ACB tolerant line.

TABLE 4

Asian corn borer assay of AH35009 seedlings under laboratory screening condition

| Line ID | Screening round | Number of larva at $1^{st}$ instar | Number of larva at $2^{nd}$ instar | Number of total observed larva | Larva growth inhibitory rate (%) | P value | P ≤ 0.01 |
|---|---|---|---|---|---|---|---|
| ZH11-TC | 1-1 | 0 | 0 | 12 | 0.00 | | |
| AH35009 | | 0 | 6 | 6 | 100.00 | 0.0000 | Y |
| ZH11-TC | 2-1 | 0 | 0 | 12 | 0.00 | | |
| AH35009 | | 0 | 11 | 12 | 91.67 | 0.0000 | Y |
| ZH11-TC | 2-2 | 0 | 0 | 12 | 0.00 | | |
| AH35009 | | 0 | 6 | 12 | 50.00 | 0.0047 | Y |
| ZH11-TC | | 0 | 0 | 9 | 0.00 | | |
| AH35009 | 3-1 | 0 | 5 | 9 | 55.56 | 0.0085 | Y |
| AH35009 | 3-2 | 0 | 1 | 9 | 11.11 | 0.3035 | |

3) AH30161 Seedlings

After ACB neonate larvae inoculating seedlings for 5 days in the screens, the seedlings of ZH11-TC were significantly damaged by ACB insects, while AH30161 seedling were less damaged, and the insects fed with AH30161 seedling was smaller than that fed with ZH11-TC control. Table 5 shows the three rounds screening results for AH30161 seedlings. In the first screening, all six insects in AH30161 seedlings' wells developed to $2^{nd}$ instar, while all observed 12 insects fed with ZH11-TC seedlings normally grew to $3^{rd}$ instar. The larva growth inhibitory rate of AH30161 (100%) was significantly greater than that of ZH11-TC seedlings (0.00%). These results indicated that AH30161 seedlings inhibited the development of ACB larva. Therefore, it was further screened. In the second screening, the larva growth inhibitory rates of AH30161 in two repeats were 88% and 67%, respectively, which were significantly greater than that of their corresponding ZH11-TC controls. The larva growth inhibitory rates of AH30161 seedlings were also significantly greater than ZH11-TC controls in the $3^{rd}$ round screening. These results clearly and consistently demonstrate that AH30161 seedling can inhibit the development of ACB insect and AH30161 was an ACB tolerant line.

TABLE 5

Asian corn borer assay of AH30161 seedlings under laboratory screening condition

| Line ID | Screening round | Number of larva at $1^{st}$ instar | Number of larva at $2^{nd}$ instar | Number of total observed larva | Larva growth inhibitory rate (%) | P value | P ≤ 0.01 |
|---|---|---|---|---|---|---|---|
| ZH11-TC | 1-1 | 0 | 0 | 12 | 0.00 | | |
| AH30161 | | 0 | 6 | 6 | 100.00 | 0.0000 | Y |
| ZH11-TC | | 0 | 0 | 12 | 0.00 | | |
| AH30161 | 2-1 | 0 | 10 | 12 | 83.33 | 0.0000 | Y |
| AH30161 | 2-2 | 0 | 8 | 12 | 66.67 | 0.0005 | Y |
| ZH11-TC | | 0 | 0 | 12 | 0.00 | | |
| AH30161 | 3-1 | 0 | 10 | 12 | 83.33 | 0.0000 | Y |
| AH30161 | 3-2 | 0 | 10 | 12 | 83.33 | 0.0000 | Y |

The results above showed that AH43610, AH35009 and AH30161 seedlings showed significant inhibitory impact on the growth and development of ACB.

Example 3

Cross-Validation of ACB Tolerance ATLs with Oriental Armyworm (*Mythimna separata*) Under Laboratory Conditions Oriental armyworm (OAW) was used in cross-validations of insecticidal activity. OAW belongs to Lepidoptera Noctuidae, and is a polyphagous insect pest. The eggs of OAW were obtained from the Institute of Plant Protection of Chinese Academy of Agricultural Sciences and hatched in an incubator at 27° C. The neonate larvae were used in this cross-validation assay.

Rice ATL plants were cultured as described in Example 2, and the experiments design was similar as to ACB insect assay described in Example 2. Five days later, all the survived larvae were visually measured and given tolerant values according to Table 2.

Larvae growth inhibitory rate was used as a parameter for this insect tolerance assay, which is the percentage of the inhibited number over the statistics number of larvae, wherein the inhibited number is the sum of the tolerance value of all observed test insects from four wells in one repeat and the statistics number of larvae is the sum of the number of all the observed insects and number of larvae at $1^{st}$ instar.

The raw data were analyzed by Chi-square, the lines with P<0.01 were considered as OAW tolerant positive lines.
Screening Results:

Table 6 shows the OAW screening results of AH43610, AH35009 and AH30161. No larva of all observed 22 larvae in four AH43610 wells developed to $3^{rd}$ instar, 15 larvae developed to $2^{nd}$ instar, and seven larvae developed to $1^{st}$ instar; while nine larvae in the ZH11-TC control wells grew to $3^{rd}$ instar, 34 larvae grew to $2^{nd}$ instar and two larvae grew to $1^{st}$ instar. The larvae growth inhibitory rate of AH43610 seedlings was 100%, which was significantly greater than that of ZH11-TC control (80.85%).

Three larvae of all observed 20 larvae in four AH35009 wells developed to $1^{st}$ instar, and 8 larvae developed to $2^{nd}$ instar; while nine larvae grew to $1^{st}$ instar and 8 larvae grew to $2^{nd}$ instar in the ZH11-TC control wells. The larvae growth inhibitory rate of AH35009 seedlings was slightly greater than that of ZH11-TC control.

Two repeats were performed for AH30161 line. The larvae growth inhibitory rate of AH30161 seedlings was greater than that of ZH11-TC control.

These results demonstrate that AH43610, AH35009 and AH30161 seedlings inhibit the growth of OAW larvae.

Two main stems of ATLs or ZH11-TC rice plants cultured for 40 days were cut into 7-8 cm, and inserted into agar in 100 mL triangular flask, and then 10 RSB neonate larvae were inoculated on the top of main stems with a brush in each triangular flask. The triangular flasks were placed in chamber with temperature at 27.5° C. and 70% relative humidity. The ZH11-TC main stems were used as control, and six repeats were designed in the experiments.

Mortality rate and larvae growth inhibitory rate were measured 7 days after inoculation. The mortality rate is the percentage of number of died larvae over the number of inoculated larvae, and the larvae growth inhibitory rate is the percentage of the sum of number of died larvae, number of larvae at $1^{st}$ instar and number of larvae at $2^{nd}$ instar over the number of inoculated larvae.

The raw data were analyzed by Chi-square, the lines with P<0.01 are considered as RSB tolerance positive lines.
Screening Results:
1) AH43610 Stems As shown in Table 7, of all the 30 RSB larvae fed with the AH43610 stems, 14 larvae died, five larvae grew to $1^{st}$ instar, and six larvae grew to $2^{nd}$ instar; while six larvae fed with ZH11-TC seedlings died, 15 larvae grew to $2^{nd}$ instar,

TABLE 6

Oriental armyworm assay of AH43610, AH35009 and AH30161 seedlings under laboratory screening condition

| Line ID | Test Round | Number of larvae at $1^{st}$ instar | Number of larvae at $2^{nd}$ instar | Number of total observed larvae | Larvae growth inhibitory rate (%) | P value | P ≤ 0.01 |
|---------|------------|-------------------------------------|-------------------------------------|---------------------------------|-----------------------------------|---------|----------|
| ZH11-TC | 1 | 2 | 34 | 45 | 80.85 | | |
| AH43610 |   | 7 | 15 | 22 | 100.00 | 0.0121 | |
| ZH11-TC | 1 | 9 | 8 | 43 | 50.00 | | |
| AH35009 |   | 3 | 8 | 20 | 60.87 | 0.6553 | |
| ZH11-TC | 1 | 0 | 8 | 40 | 20.00 | | |
| AH30161 |   | 0 | 6 | 20 | 30.00 | 0.3919 | |
| ZH11-TC | 2 | 1 | 20 | 34 | 62.86 | | |
| AH30161 |   | 4 | 10 | 16 | 90.00 | 0.0093 | Y |

Example 4

Cross-Validation of ACB Tolerance Positive ATLs with Rice Stem Bore (*Chilo suppressalis*) Under Laboratory Screening Conditions Rice stem borer (RCB) belongs to Lepidoptera Pyralidae and it is a very important rice pest. They infest plants from the seedling stage to maturity. Although worldwide in distribution, rice stem borers are particularly destructive in Asia, the Middle East, and the Mediterranean regions.

The eggs of RSB were obtained from the Institute of Plant Protection of Chinese Academy of Agricultural Sciences and hatched in an incubator at 27° C. The neonate larvae were used in this cross-validation assay.

ATLs seedlings were cultured in greenhouse. Two types of lamps were provided as light source, i.e. sodium lamp and metal halide lamp, with the ratio of 1:1. Lamps provide the 16 h/8 h period of day/night, and were placed approximately 1.5 m above the seedbed. The light intensity 30 cm above the seedbed is measured as 10,000-20,000 lx in sunny day, while 6,000-10,000 lx in cloudy day, the relative humidity ranges from 30% to 90%, and the temperature ranges from 20 to 35° C. The tillered seedlings cultured with modified IRRI nutrient solution for 40 days were used in this assay.
Screening Method:

and three larvae grew to $1^{st}$ instar. The mortality rate and larvae growth inhibitory rate of AH43610 main stems were 46.67% and 83.33%, respectively. The mortality rate and larvae growth inhibitory rate of ZH11-TC controls were 15% and 60%, respectively. These results clearly show that AH43610 can inhibit the growth and development of RSB larvae.

2) AH35009 Stems

For AH35009 stems fed RSB larvae, 49 larvae died, six larvae developed to $1^{St}$ instar and five larvae developed to $2^{nd}$ instar; whereas eight larvae fed with ZH11-TC controls died, and five larvae developed to $2^{nd}$ instar. The mortality rate and larvae growth inhibitory rate of AH35009 main stems were greater than that of ZH11-TC main stems, indicating that AH35009 seedlings can inhibit the growth of RSB larvae.

3) AH30161 Stems

For AH30161 stems fed RSB larvae, 16 larvae died, 11 larvae developed to $1^{st}$ instar and 14 larvae developed to $2^{nd}$ instar; whereas eight larvae fed with ZH11-TC controls died, and five larvae developed to $2^{nd}$ instar. The mortality rate and larvae growth inhibitory rate of AH30161 main stems were greater than that of ZH11-TC main stems, indicating that AH30161 seedlings can inhibit the growth of RSB larvae.

TABLE 7

Rice stem borer assay of AH43610, AH35009 and AH30161 seedlings under laboratory screening condition

| Line ID | Number of dead larvae | Number of 1st instar | Number of 2nd instar | Number of total larvae | Mortality rate (%) | P value | Inhibited rate (%) | P value |
|---|---|---|---|---|---|---|---|---|
| ZH11-TC | 6 | 3 | 15 | 40 | 15.00 | | 60.00 | |
| AH43610 | 14 | 5 | 6 | 30 | 46.67 | 0.1268 | 83.33 | 0.2108 |
| ZH11-TC | 8 | 0 | 5 | 60 | 13.33 | | 21.67 | |
| AH35009 | 49 | 6 | 5 | 60 | 81.67 | 0.000 | 100.00 | 0.000 |
| ZH11-TC | 8 | 0 | 5 | 60 | 13.33 | | 21.67 | |
| AH30161 | 16 | 11 | 14 | 60 | 26.70 | | 68.30 | |

AH43610, AH35009 and AH30161 seedlings showed significant inhibitory impact on the growth and development of ACB, OAW and RSB insects, indicating the potential broad spectrum of insecticidal activities.

In light of these results, the gene(s) which contributed to the enhanced insect tolerance of Line AH43610, AH35009 and AH30161 were isolated.

Example 5

Identification of Activation-Tagged Genes

Genes flanking the T-DNA insertion locus in the insect tolerant line AH43610, AH35009 and AH30161 were identified.

Genomic DNA was isolated from leaf tissues of AH43610 line, AH35009 line and AH30161 line using CTAB method (Murray, M. G. and W. F. Thompson. (1980) *Nucleic Acids Res.* 8: 4321-4326). The flanking sequences of T-DNA insertion locus were obtained by molecular technology.

The T-DNA inserted in chromosome 1 of AH35009 line (MSU7.0 http://rice.plantbiology.msu.edu/index.shtml). The nucleotide sequence of RB and LB flanking sequence of T-DNA in AH35009 is shown in SEQ ID NO: 1 and 2.

The T-DNA inserted in chromosome 9 of AH30161 (MSU7.0 http://rice.plantbiology.msu.edu/index.shtml). The nucleotide sequence of LB flanking sequence of T-DNA in AH30161 is shown in SEQ ID NO: 3.

The genes near the insertion locus were cloned and validated as to its functions in insect tolerance and other agronomic trait improvement.

Example 6

Insect Tolerance Genes Cloning and Over-Expression Construct Construction

Based on the sequence information of gene ID (LOC_Os03g16910.1, LOC_Os01g53730.1 and LOC_Os09g10010.1), primers were designed for cloning rice insect tolerance genes. The primers and the expected-lengths of the amplified genes are shown in Table 8.

OsSLT1, OsDN-ITP6 and OsDN-ITP7 cDNA were cloned from pooled cDNA from leaf, stem and root tissues of Zhonghua11 plant using conventional method.

TABLE 8

Primers for cloning insect tolerance genes

| Primer | Sequence | SEQ ID NO: | Gene name | Length of amplified fragment (bp) |
|---|---|---|---|---|
| gc-4343 | 5'-CTGCTGAGG GTGGAGAGATTT GGAGGAGAGGA G-3' | 13 | OsSLT1 | 1806 |
| gc-4344 | 5'-CCGCTGAGG CACACACCTTGA ACATGTTAAGAC TG-3' | 14 | | |
| gcl-1868 | 5'-ATACACAAA GCGTACCTGTTC TTTCG-3' | 15 | OsDN-ITP6 | 600 |
| gcl-1869 | 5'-CGATACTGT TCCTACTGATGA TATCCG-3' | 16 | | |
| gcl-0873 | 5'-CTGCTGAGG TGGAAGTGGAGC AAGGTTGAGTTA C-3' | 17 | OsDN-ITP7 | 244 |
| gcl-0874 | 5'-CCGCTGAGG AACTAGTTGTTC ACAAGGCAGCA G-3' | 18 | | |

The PCR amplified products were extracted after the agarose gel electrophoresis using a column kit and then ligated with TA cloning vectors. The sequence and orientation in the construct was confirmed by sequencing. The genes were cloned into plant binary construct DP0158 (pCAMBIA1300-DsRed) (publication No. WO 2016/000237). The cloned nucleotide sequence in construct of DP1672 and coding sequence of OsSLT1 are provided as SEQ ID NO: 4 and 5, the encoded amino acid sequence of OsSLT1 is SEQ ID NO: 6; the cloned nucleotide sequence in construct of DP1759 and coding sequence of OsDN-ITP6 are provided as SEQ ID NO: 7 and 8, the encoded amino acid sequence of OsDN-ITP6 is SEQ ID NO: 9; and the cloned nucleotide sequence in construct of DP1791 and coding sequence of OsDN-ITP7 are provided as SEQ ID NO: 10 and 11, the encoded amino acid sequence of OsDN-ITP7 is SEQ ID NO: 12.

47

Example 7

Transformation of Transgenic Rice Lines

The over-expression constructs and empty vectors (DP0158) were transformed into Zhonghua 11 (*Oryza sativa* L.) by Agrobacteria-mediated method as described by Lin and Zhang ((2005) *Plant Cell Rep.* 23:540-547). The transgenic seedlings (T0) generated in transformation laboratory were transplanted in the field to get T1 seeds. The T1 and T2 seeds were stored at cold room (4° C.). The over-expression constructs contain DsRED and HYG genes. T1 and T2 seeds which showed red color under green fluorescent light were transgenic seeds and were used in the following insect tolerant assays.

Gene Expression Analysis in Transgenic Rice Plants:

Gene expression levels in the transgenic rice plants were analyzed by a standard real-time RT-PCR procedure. EF1α gene was used as an internal control to show that the amplification and loading of samples from the transgenic rice and control plant were similar. The expression level was normalized based on the EF1α mRNA levels.

The relative expression levels of OsSLT1 gene in leaves of different DP1672 transgenic rice lines were determined by real-time PCR analyses, and the expression levels in the OsSLT1 lines ranged from about 1.21-7.63-fold-increases compared to ZH11-TC. The primers for real-time RT-PCR for the OsSLT1 gene in the over-expression transgenic rice are listed below:

```
DP1672-F1:
                                        (SEQ ID NO: 19)
5'-CGGACCTTCAAGTTAGTCGATC-3'

DP1672-R1:
                                        (SEQ ID NO: 20)
5'-CCGAGTAGGGAGTGGAATTTC-3'
```

The relative expression levels of OsDN-ITP6 gene in leaves of different DP1759 transgenic rice lines were determined by real-time PCR analyses and ranged from about 2.38-15.71 as compared to the base expression level in ZH11-TC (set at 1.00). OsDN-ITP6 over-expressed in almost all the tested transgenic rice lines. The primers used for the real-time PCR are as below:

```
DP1759-F1:
                                        (SEQ ID NO: 21)
5'-CTATGTAGCACTGGATGGGAAC-3'

DP1759-R1:
                                        (SEQ ID NO: 22)
5'-GCTTTTGGTGTTATTCCTGGC-3'
```

The relative expression levels of OsDN-ITP7 gene in leaves of different DP1791 transgenic rice lines were determined by real-time PCR analyses and ranged from about 95-591 as compared to the base expression level in ZH11-TC (set at 1.00). OsDN-ITP7 over-expressed in almost all the tested transgenic rice lines.

```
DP1791-F1:
                                        (SEQ ID NO: 23)
5'-TGCTATTTCAGACTTAGGCCG-3'

DP1791-R1:
                                        (SEQ ID NO: 24)
5'-AAGGCAGCAGTTCTCATCG-3'
```

48

Example 8

ACB Assay of OsSLT1 Transgenic Rice Plants Under Laboratory Conditions

In order to investigate whether OsSLT1 transgenic rice can recapitulate the insect tolerance trait of AH43610 line, the OsSLT1 transgenic rice was first tested against ACB insect. The ACB insect was reared as described in Example 2.

T2 plants generated with the construct were tested in the assays for about three times with four to six repeats. The seedlings of ZH11-TC and DP0158 were used as controls. About ten lines transgenic rice were tested and 450 seeds of each line were water cultured for 10 days as described in Example 2. This recapitulation assay used randomized block design. Seedlings of each line were inserted in two wells of the 32-well-plate, and ZH11-TC and DP0158 seedlings were inserted in six different wells in the same plate.

Larva growth inhibitory rate was used as a parameter for ACB insect tolerance assay, which is the percentage of the inhibited larva number over the statistics number of larva, wherein the inhibited larva number is the sum of the tolerance value of test insects from wells and the statistics number of larva is the sum of the number of all the observed insects and number of larva at $1^{st}$ instar.

Randomized block design was used, and ten transgenic lines from a construct were tested in one experimental unit to evaluate the gene function by SAS PROC GLIMMIX considering construct, line and environment effects. If the larva growth inhibitory rates of the transgenic rice plants at both construct and line levels were significantly greater than controls ($P<0.05$), the gene was considered having ACB tolerant function.

ACB Screening Results:

1) Results of the First Validation Experiment

After ACB neonate larvae inoculating seedlings for 5 days in the assays, the seedlings of ZH11-TC and DP0158 were significantly damaged by ACB insects, while the OsSLT1 transgenic seedlings were less damaged, and the insects fed with the OsSLT1 transgenic seedlings was smaller than that fed with ZH11-TC and DP0158 controls.

Ten OsSLT1 transgenic lines were placed on one plate, and repeated for five times. A total of 600 ACB neonate larvae were inoculated on OsSLT1 transgenic rice seedlings. Five days after inoculation, 333 larvae were found, 38 larvae developed to $1^{st}$ instar, and 111 larvae developed to $2^{nd}$ instar. Eight larvae in ZH11-TC seedlings' wells developed to $1^{st}$ instar, and 23 larvae developed to $2^{nd}$ instar. Similar results were obtained with DP0158 seedlings, 9 larvae developed to $1^{st}$ instar and 17 larvae developed to $2^{nd}$ instar. The average larva growth inhibitory rates of OsSLT1 transgenic rice, ZH11-TC and DP0158 were 50%, 28% and 24%, respectively. The average larva growth inhibitory rate of OsSLT1 transgenic rice was significantly greater than that of ZH11-TC and DP0158 controls. These results show that over-expression of OsSLT1 in rice significantly increased ACB insect tolerance of transgenic rice at construct level.

Further analysis at transgenic line level is displayed in Table 9. Eight transgenic lines exhibited significantly greater larva growth inhibitory rates than both ZH11-TC and DP0158 controls. These results further indicate OsSLT1 plays a role in increasing ACB insect tolerance in rice compared to controls at line level.

TABLE 9

Asian corn borer assay of OsSLT1 transgenic rice under laboratory screening condition at line level (1$^{st}$ experiment)

| Line ID | Number of larva at 1$^{st}$ instar | Number of larvae at 2$^{nd}$ instar | Number of total observed larvae | Larvae growth inhibitory rate (%) | CK = ZH11-TC P value | P ≤ 0.05 | CK = DP0158 P value | P ≤ 0.05 |
|---|---|---|---|---|---|---|---|---|
| DP1672 (Construct) | 38 | 111 | 333 | 50.40 | 0.0000 | Y | 0.0000 | Y |
| ZH11-TC | 8 | 23 | 129 | 28.47 | | | | |
| DP0158 | 9 | 17 | 135 | 24.31 | | | | |
| DP1672.02 | 4 | 14 | 26 | 73.33 | 0.0000 | Y | 0.0000 | Y |
| DP1672.03 | 5 | 20 | 45 | 60.00 | 0.0003 | Y | 0.0000 | Y |
| DP1672.05 | 4 | 13 | 33 | 56.76 | 0.0028 | Y | 0.0005 | Y |
| DP1672.06 | 4 | 7 | 22 | 57.69 | 0.0073 | Y | 0.0009 | Y |
| DP1672.07 | 3 | 18 | 42 | 53.33 | 0.0042 | Y | 0.0007 | Y |
| DP1672.08 | 2 | 19 | 46 | 47.92 | 0.0084 | Y | 0.0037 | Y |
| DP1672.09 | 3 | 2 | 26 | 27.59 | 0.9285 | | 0.7040 | |
| DP1672.11 | 4 | 4 | 18 | 54.55 | 0.0205 | Y | 0.0068 | Y |
| DP1672.12 | 6 | 6 | 27 | 54.55 | 0.0078 | Y | 0.0007 | Y |
| DP1672.15 | 3 | 8 | 48 | 27.45 | 0.9026 | | 0.6450 | |

2) Results of the Second Validation Experiment

The same ten OsSLT1 transgenic lines were tested in this second experiment with five repeats. Five days after inoculation, 389 larvae were found, 22 larvae developed to 1$^{st}$ instar, and 94 larvae developed to 2$^{nd}$ instar. Only six larvae of all the observed 144 larvae in ZH11-TC seedling's wells developed to 1$^{st}$ instar, 17 larvae developed to 2$^{nd}$ instar. Three larvae in DP0158 seedlings' wells developed to 1$^{St}$ instar and 22 larvae developed to 2$^{nd}$ instar. The average larva growth inhibitory rates of OsSLT1 transgenic rice, ZH11-TC and DP0158 were 34%, 19% and 18%, respectively. The average larva growth inhibitory rate of OsSLT1 transgenic rice was significantly greater than that of ZH11-TC and DP0158 controls. These results show that over-expression of OsSLT1 in rice increased ACB insect tolerance of transgenic rice at construct level.

Further analysis at transgenic line level is displayed in Table 10. Eight transgenic lines exhibited greater larva growth inhibitory rates than both ZH11-TC and DP0158 seedlings, and four lines exhibited the significantly greater larva growth inhibitory rates. The result was similar to that in the first validation experiment. These results further indicate OsSLT1 plays a role in increasing ACB insect tolerance in rice compared to controls at line level.

TABLE 10

Asian corn borer assay of OsSLT1 transgenic rice under laboratory screen condition at line level (2$^{nd}$ experiment)

| Line ID | Number of larva at 1$^{st}$ instar | Number of larvae at 2$^{nd}$ instar | Number of total observed larvae | Larvae growth inhibitory rate (%) | CK = ZH11-TC P value | P ≤ 0.05 | CK = DP0158 P value | P ≤ 0.05 |
|---|---|---|---|---|---|---|---|---|
| DP1672 (Construct) | 22 | 94 | 389 | 33.58 | 0.0400 | Y | 0.0236 | Y |
| ZH11-TC | 6 | 17 | 144 | 19.33 | | | | |
| DP0158 | 3 | 22 | 149 | 18.42 | | | | |
| DP1672.02 | 3 | 3 | 22 | 36.00 | 0.0713 | | 0.0547 | |
| DP1672.03 | 5 | 20 | 53 | 51.72 | 0.0000 | Y | 0.0000 | Y |
| DP1672.05 | 2 | 19 | 48 | 46.00 | 0.0006 | Y | 0.0004 | Y |
| DP1672.06 | 1 | 3 | 24 | 20.00 | 0.9381 | | 0.8516 | |
| DP1672.07 | 4 | 17 | 50 | 46.30 | 0.0004 | Y | 0.0002 | Y |
| DP1672.08 | 1 | 13 | 46 | 31.91 | 0.0786 | | 0.0569 | |
| DP1672.09 | 0 | 2 | 34 | 5.88 | 0.0809 | | 0.0952 | |
| DP1672.11 | 2 | 5 | 21 | 39.13 | 0.0417 | Y | 0.0315 | Y |
| DP1672.12 | 0 | 4 | 27 | 14.81 | 0.5823 | | 0.6548 | |
| DP1672.15 | 4 | 8 | 64 | 23.53 | 0.4814 | | 0.3856 | |

3) Results of the Third Validation Experiment

The third experiment was performed with five repeats. Five days after inoculation, 287 larvae were found in the OsSLT1 transgenic seedlings' wells, 32 larvae developed to 1$^{st}$ instar, and 106 larvae developed to 2$^{nd}$ instar. 12 larvae in ZH11-TC seedling's wells developed to 1$^{st}$ instar, and 45 larvae developed to 2$^{nd}$ instar, and 14 larvae in DP0158 seedlings' wells developed to 1$^{st}$ instar, and 39 larvae developed to 2$^{nd}$ instar. The average larva growth inhibitory rates of OsSLT1 transgenic rice, ZH11-TC and DP0158 were 53%, 41% and 45%, respectively. The average larva growth inhibitory rate of OsSLT1 transgenic rice was significantly greater than that of ZH11-TC control. These results also show that over-expression of OsSLT1 in rice increased ACB insect tolerance of transgenic rice at construct level.

Further analysis at transgenic line level is displayed in Table 11. Eight transgenic lines exhibited greater larva growth inhibitory rates than both ZH11-TC and DP0158 seedlings. Three transgenic lines exhibited significantly greater larva growth inhibitory rates than both ZH11-TC and DP0158 seedlings. These results consistently further indicate OsSLT1 plays a role in increasing ACB insect tolerance in rice compared to controls at line level.

one 32-well plate with five repeats. Five days after co-culture, 445 larvae were found in the OsSLT1 transgenic rice wells, wherein six larvae developed to $1^{st}$ instar and 118 OAW larvae developed to $2^{nd}$ instar, while five of the 215 larvae in the ZH11-TC wells developed to $1^{st}$ instar, 37 larvae developed to $2^{nd}$ instar; and one of 218 larvae in the

TABLE 11

Asian corn borer assay of OsSTL1 transgenic rice under laboratory screen condition at line level ($3^{rd}$ experiment)

| Line ID | Number of larva at $1^{st}$ instar | Number of larva at $2^{nd}$ instar | Number of total observed larva | Larva growth inhibitory rate (%) | CK = ZH11-TC P value | P ≤ 0.05 | CK = DP0158 P value | P ≤ 0.05 |
|---|---|---|---|---|---|---|---|---|
| DP1672 (Construct) | 32 | 106 | 287 | 53.29 | 0.0037 | Y | 0.0755 | |
| ZH11-TC | 12 | 45 | 157 | 40.83 | | | | |
| DP0158 | 14 | 39 | 134 | 45.27 | | | | |
| DP1672.02 | 2 | 11 | 25 | 55.56 | 0.1287 | | 0.3305 | |
| DP1672.03 | 12 | 7 | 36 | 64.58 | 0.0038 | Y | 0.0248 | Y |
| DP1672.05 | 3 | 15 | 29 | 65.63 | 0.0104 | Y | 0.0441 | Y |
| DP1672.06 | 5 | 7 | 17 | 77.27 | 0.0030 | Y | 0.0103 | Y |
| DP1672.07 | 4 | 12 | 28 | 62.50 | 0.0223 | Y | 0.0852 | |
| DP1672.08 | 1 | 18 | 41 | 47.62 | 0.3521 | | 0.7884 | |
| DP1672.09 | 2 | 4 | 25 | 29.63 | 0.3266 | | 0.1407 | |
| DP1672.11 | 0 | 11 | 22 | 50.00 | 0.3585 | | 0.6795 | |
| DP1672.12 | 1 | 8 | 17 | 55.56 | 0.2025 | | 0.4141 | |
| DP1672.15 | 2 | 13 | 47 | 34.69 | 0.5332 | | 0.2008 | |

Example 9

OAW Assay of OsSLT1 Transgenic Rice Plants under Laboratory Conditions OAW assay of OsSLT1 transgenic rice were performed as described in Example 3. Larva growth inhibitory rate was used as a parameter for this insect tolerance assay, which is the percentage of the inhibited number over the statistics number of larvae, wherein the inhibited number is the sum of the tolerance value of all observed test insects from ten to twelve wells and the statistics number of larvae is the sum of the number of all the observed insects and number of larvae at $1^{st}$ instar.

OAW Screening Results:

Ten OsSLT1 transgenic rice lines tested in ACB assay were tested in OAW assay. These ten lines were placed on DP0158 wells developed to $1^{st}$ instar, and 35 developed to $2^{nd}$ instar. The average OAW larvae growth inhibitory rates of OsSLT1 transgenic rice, ZH11-TC and DP0158 were 29%, 21% and 17%. The OAW larvae growth inhibitory rate of OsSLT1 transgenic rice was greater than ZH11-TC control and significantly greater than DP0158 control.

Analysis at line level was shown in Table 12. Six lines had greater larvae growth inhibitory rates than both ZH11-TC and DP0158 controls. Four lines had significantly greater inhibitory rates than ZH11-TC and DP0158 controls. These results demonstrate that OsSLT1 transgenic rice had improved OAW tolerance at seedling stage.

TABLE 12

Armyworm assay of OsSLT1 transgenic rice under laboratory screening condition at line level

| Line ID | Number of larva at $1^{st}$ instar | Number of larva at $2^{nd}$ instar | Number of total observed larvae | Larva growth inhibitory rate (%) | CK = ZH11-TC P value | P ≤ 0.05 | CK = DP0158 P value | P ≤ 0.05 |
|---|---|---|---|---|---|---|---|---|
| DP1672 (Construct) | 6 | 118 | 445 | 28.82 | 0.2469 | | 0.0218 | Y |
| ZH11-TC | 5 | 37 | 215 | 21.36 | | | | |
| DP0158 | 1 | 35 | 218 | 16.89 | | | | |
| DP1672.02 | 0 | 5 | 29 | 17.24 | 0.3395 | | 0.6667 | |
| DP1672.03 | 1 | 6 | 50 | 15.69 | 0.2579 | | 0.6371 | |
| DP1672.05 | 1 | 19 | 55 | 37.50 | 0.0213 | Y | 0.0026 | Y |
| DP1672.06 | 0 | 20 | 28 | 71.43 | 0.0001 | Y | 0.0001 | Y |
| DP1672.07 | 2 | 18 | 58 | 36.67 | 0.0252 | Y | 0.0030 | Y |
| DP1672.08 | 0 | 12 | 55 | 21.82 | 0.9820 | | 0.4753 | |
| DP1672.09 | 0 | 4 | 42 | 9.52 | 0.0484 | | 0.1396 | |
| DP1672.11 | 1 | 7 | 28 | 31.03 | 0.4559 | | 0.1812 | |
| DP1672.12 | 0 | 11 | 55 | 20.00 | 0.7437 | | 0.6897 | |
| DP1672.15 | 1 | 16 | 45 | 39.13 | 0.0335 | Y | 0.0052 | Y |

Example 10

ACB Assay of OsDN-ITP6 Transgenic Rice Plants Under Laboratory Conditions

In order to investigate whether OsDN-ITP6 transgenic rice can recapitulate the insect tolerance trait of AH35009 line, the OsDN-ITP6 transgenic rice was tested against ACB insect. The method is described in Example 8.

ACB Screening Results:

1) Results of First Validation Experiment

After ACB neonate larvae inoculating seedlings for 5 days in the assays, the seedlings of ZH11-TC and DP0158 were significantly damaged by ACB insects, while the OsDN-ITP6 transgenic seedlings were less damaged, and the insects fed with the OsDN-ITP6 transgenic seedlings was smaller than that fed with ZH11-TC and DP0158 controls.

Seven OsDN-ITP6 transgenic lines were placed on one 32-well plate with five repeats. A total of 330 ACB neonate larvae were found in OsDN-ITP6 transgenic seedlings wells, wherein 2 larvae developed to $1^{st}$ instar and 108 larvae developed to $2^{nd}$ instar, the average larva growth inhibitory rate was 34%; while 155 larvae were found in ZH11-TC seedling wells, 31 larvae developed to $2^{nd}$ instar; and 21 larvae of all observed 138 larvae inoculated on the DP0158 seedling developed to $2^{nd}$ instar. The average larva growth inhibitory rates of ZH11-TC seedlings and DP0158 seedling were 20% and 15%, respectively. The average larva growth inhibitory rate of OsDN-ITP6 transgenic rice was significantly greater than that of ZH11-TC control and DP0158 control. These results demonstrate that over-expression of OsDN-ITP6 increased ACB insect tolerances of transgenic rice at construct level.

Further analysis at transgenic line level is displayed in Table 13. All the seven transgenic rice plants showed greater larva growth inhibitory rates than ZH11-TC and DP0158 seedlings. Two lines showed significantly greater larvae growth inhibitory rates than ZH11-TC control, and five lines exhibited significantly greater larvae growth inhibitory rates than DP0158 seedlings. These results demonstrate that OsDN-ITP6 transgenic rice showed inhibitory impact on ACB larval growth and OsDN-ITP6 plays a role in increasing ACB insect tolerance of transgenic rice seedlings at construct and line levels.

TABLE 13

Asian corn borer assay of OsDN-ITP6 transgenic rice under laboratory screening condition at line level ($1^{st}$ experiment)

| Line ID | Number of larva at $1^{st}$ instar | Number of larva at $2^{nd}$ instar | Number of total observed larvae | Larvae growth inhibitory rate (%) | CK = ZH11-TC P value | CK = ZH11-TC P ≤ 0.05 | CK = DP0158 P value | CK = DP0158 P ≤ 0.05 |
|---|---|---|---|---|---|---|---|---|
| DP1759 (Construct) | 2 | 108 | 330 | 33.73 | 0.0036 | Y | 0.0002 | Y |
| ZH11-TC | 0 | 31 | 155 | 20.00 | | | | |
| DP0158 | 0 | 21 | 138 | 15.22 | | | | |
| DP1759.07 | 0 | 13 | 49 | 26.53 | 0.3379 | | 0.0861 | |
| DP1759.08 | 1 | 15 | 52 | 32.08 | 0.0790 | | 0.0128 | Y |
| DP1759.09 | 0 | 22 | 46 | 47.83 | 0.0005 | Y | <.0001 | Y |
| DP1759.10 | 0 | 17 | 44 | 38.64 | 0.0149 | Y | 0.0020 | Y |
| DP1759.12 | 1 | 16 | 56 | 31.58 | 0.0834 | | 0.0132 | Y |
| DP1759.14 | 0 | 12 | 43 | 27.91 | 0.2723 | | 0.0683 | |
| DP1759.15 | 0 | 13 | 40 | 32.50 | 0.1001 | | 0.0197 | Y |

2) Results of Second Validation Experiment

The same seven OsDN-ITP6 transgenic lines were placed on one 32-well plate with six repeats. A total of 382 ACB neonate larvae were found in OsDN-ITP6 transgenic seedlings wells, wherein 27 larvae developed to $1^{st}$ instar and 169 larvae developed to $2^{nd}$ instar, the average larva growth inhibitory rate was 55%; while four larvae in ZH11-TC seedling wells developed to $1^{st}$ instar, and 38 larvae developed to $2^{nd}$ instar; and two larvae in DP0158 seedling wells developed to $1^{st}$ instar, and 37 larvae developed to $2^{nd}$ instar. The average larva growth inhibitory rates of ZH11-TC seedlings and DP0158 seedlings were 41% and 34%. The average larva growth inhibitory rate of OsDN-ITP6 transgenic rice was significantly greater than that of ZH11-TC control and DP0158 control. These results demonstrate that over-expression of OsDN-ITP6 increased ACB insect tolerances of transgenic rice seedlings at construct level.

Further analysis at transgenic line level is displayed in Table 14. All the seven lines had significantly greater larva growth inhibitory rates than DP0158 control; and one transgenic line had significantly greater larva growth inhibitory rates than ZH11-TC control. These results demonstrate that OsDN-ITP6 transgenic rice showed inhibitory impact on ACB larval growth and OsDN-ITP6 plays a role in increasing ACB insect tolerance of transgenic rice seedlings at construct and line levels.

TABLE 14

Asian corn borer assay of OsDN-ITP6 transgenic rice under laboratory screening condition at line level (2$^{nd}$ experiment)

| Line ID | Number of larva at 1$^{st}$ instar | Number of larva at 2$^{nd}$ instar | Number of total observed larvae | Larvae growth inhibitory rate (%) | CK = ZH11-TC P value | P ≤ 0.05 | CK = DP0158 P value | P ≤ 0.05 |
|---|---|---|---|---|---|---|---|---|
| DP1759 (Construct) | 27 | 169 | 382 | 54.52 | 0.0133 | Y | 0.0001 | Y |
| ZH11-TC | 4 | 38 | 107 | 41.44 | | | | |
| DP0158 | 2 | 37 | 118 | 34.17 | | | | |
| DP1759.07 | 3 | 27 | 56 | 55.93 | 0.0939 | | 0.0075 | Y |
| DP1759.08 | 7 | 25 | 55 | 62.90 | 0.0067 | Y | 0.0003 | Y |
| DP1759.09 | 6 | 16 | 50 | 50.00 | 0.2154 | | 0.0254 | Y |
| DP1759.10 | 2 | 28 | 55 | 56.14 | 0.0719 | | 0.0055 | Y |
| DP1759.12 | 3 | 27 | 56 | 55.93 | 0.0730 | | 0.0054 | Y |
| DP1759.14 | 2 | 25 | 55 | 50.88 | 0.1955 | | 0.0217 | Y |
| DP1759.15 | 4 | 21 | 55 | 49.15 | 0.2735 | | 0.0347 | Y |

3) Results of Third Validation Experiment

The third validation experiment was performed. A total of 384 ACB neonate larvae were found in OsDN-ITP6 transgenic seedlings wells, wherein 32 larvae developed to 1$^{st}$ instar and 103 larvae developed to 2$^{nd}$ instar, the average larva growth inhibitory rate was 40%; while 11 of the 169 larvae in ZH11-TC seedling wells developed to 1$^{st}$ instar, and 41 larvae developed to 2$^{nd}$ instar; and five larvae of all observed 164 larvae inoculated on the DP0158 seedling developed to 1$^{st}$ instar, and 24 larvae developed to 2$^{nd}$ instar. The average larva growth inhibitory rates of ZH11-TC seedlings and DP0158 seedling were 35% and 20%, respectively. The average larva growth inhibitory rate of OsDN-ITP6 transgenic rice was greater than ZH11-TC control and significantly greater than DP0158 control. These results demonstrate that over-expression of OsDN-ITP6 increased ACB insect tolerances of transgenic rice at construct level.

Further analysis at transgenic line level is displayed in Table 15. Five lines showed greater larva growth inhibitory rates than ZH11-TC and DP0158 seedlings. These results demonstrate that OsDN-ITP6 transgenic rice showed inhibitory impact on ACB larval growth and OsDN-ITP6 plays a role in increasing ACB insect tolerance of transgenic rice seedlings at construct and line levels.

Example 11

OAW Assay of OsDN-ITP6 Transgenic Rice Plants Under Laboratory Conditions

OAW assay of OsDN-ITP6 transgenic rice was performed as described in Example 3. The screening results as below.

OAW Screening Results:

Eight OsDN-ITP6 transgenic rice lines were tested in OAW assay. These eight lines were placed on one 32-well plate with six repeats. Five days after co-culture, 532 larvae were found in the OsDN-ITP6 transgenic rice wells, wherein two larvae developed to 1$^{st}$ instar and 195 OAW larvae developed to 2$^{nd}$ instar, while 22 of the 203 larvae in the ZH11-TC wells developed to 2$^{nd}$ instar; and 19 of 229 larvae in the DP0158 wells developed to 2$^{nd}$ instar. The average OAW larvae growth inhibitory rates of OsDN-ITP6 transgenic rice, ZH11-TC and DP0158 were 37%, 11% and 9%. The OAW larvae growth inhibitory rate of OsDN-ITP6 transgenic rice was significantly greater than ZH11-TC and DP0158 controls.

Analysis at line level was shown in Table 16. Eight lines had significantly greater larvae growth inhibitory rates than both ZH11-TC and DP0158 controls. These results demonstrate that OsDN-ITP6 transgenic rice had improved OAW tolerance at seedling stage.

TABLE 15

Asian corn borer assay of OsDN-ITP6 transgenic rice under laboratory screening condition at line level (3$^{rd}$ experiment)

| Line ID | Number of larva at 1$^{st}$ instar | Number of larva at 2$^{nd}$ instar | Number of total observed larvae | Larvae growth inhibitory rate (%) | CK = ZH11-TC P value | P ≤ 0.05 | CK = DP0158 P value | P ≤ 0.05 |
|---|---|---|---|---|---|---|---|---|
| DP1759 (Construct) | 32 | 103 | 384 | 40.14 | 0.2132 | | 0.0000 | Y |
| ZH11-TC | 11 | 41 | 169 | 35.00 | | | | |
| DP0158 | 5 | 24 | 164 | 20.12 | | | | |
| DP1759.07 | 6 | 20 | 65 | 45.07 | 0.1412 | | 0.0197 | Y |
| DP1759.08 | 1 | 18 | 54 | 36.36 | 0.8696 | | 0.0000 | Y |
| DP1759.09 | 10 | 8 | 38 | 58.33 | 0.0047 | Y | 0.0032 | Y |
| DP1759.10 | 3 | 14 | 44 | 42.55 | 0.3480 | | 0.0002 | Y |
| DP1759.12 | 5 | 18 | 54 | 47.46 | 0.0919 | | 0.3819 | |
| DP1759.14 | 5 | 15 | 75 | 31.25 | 0.5578 | | 0.4441 | |
| DP1759.15 | 2 | 10 | 54 | 25.00 | 0.1712 | | 0.1963 | |

TABLE 16

Armyworm assay of OsDN-ITP6 transgenic rice under laboratory screening condition at line level (1$^{st}$ experiment)

| Line ID | Number of larva at 1$^{st}$ instar | Number of larva at 2$^{nd}$ instar | Number of total observed larvae | Larvae growth inhibitory rate (%) | CK = ZH11-TC P value | CK = ZH11-TC P ≤ 0.05 | CK = DP0158 P value | CK = DP0158 P ≤ 0.05 |
|---|---|---|---|---|---|---|---|---|
| DP1759 (Construct) | 2 | 195 | 532 | 37.27 | 0.0000 | Y | 0.0000 | Y |
| ZH11-TC | 0 | 22 | 203 | 10.84 | | | | |
| DP0158 | 0 | 19 | 220 | 8.64 | | | | |
| DP1759.03 | 1 | 17 | 63 | 29.69 | 0.0008 | Y | 0.0000 | Y |
| DP1759.07 | 0 | 31 | 69 | 44.93 | 0.0000 | Y | 0.0000 | Y |
| DP1759.08 | 0 | 28 | 71 | 39.44 | 0.0000 | Y | 0.0000 | Y |
| DP1759.09 | 0 | 33 | 68 | 48.53 | 0.0000 | Y | 0.0000 | Y |
| DP1759.10 | 0 | 28 | 60 | 46.67 | 0.0000 | Y | 0.0000 | Y |
| DP1759.12 | 1 | 25 | 68 | 39.13 | 0.0000 | Y | 0.0000 | Y |
| DP1759.14 | 0 | 16 | 72 | 22.22 | 0.0209 | Y | 0.0039 | Y |
| DP1759.15 | 0 | 17 | 61 | 27.87 | 0.0022 | Y | 0.0003 | Y |

The transgenic lines were tested again. In the second experiment, five days later after inoculation of OAW neonate larvae, 502 larvae were found in the OsDN-ITP6 transgenic rice well, 20 larvae grew to 1$^{st}$ instar and 276 larvae grew to 2$^{nd}$ instar. The larvae growth inhibitory rate was 61%. Whereas, one larva of 154 in the ZH11-TC seedling wells grew to 1$^{st}$ instar, and 72 larvae grew to 2$^{nd}$ instar, and three larvae of the 145 larvae in DP0158 seedling wells grew to 1$^{st}$ instar and 56 larvae grew to 2$^{nd}$ instar. The OAW larvae growth inhibitory rate of OsDN-ITP6 transgenic rice was significantly greater than ZH11-TC and DP0158 controls. These results indicate that OsDN-ITP6 transgenic rice exhibited OAW larvae tolerance at construct level.

Analysis at line level shows that six lines had the larvae growth inhibitory rates more than 60%, which were significantly greater than both ZH11-TC and DP0158 controls (Table 17). These results further confirm that over-expression OsDN-ITP6 enhanced tolerance against OAW insect in transgenic rice plants, and OsDN-ITP6 plays a role in increasing OAW insect tolerance.

Example 12

ACB Assay of OsDN-ITP7 Transgenic Rice Plants Under Laboratory Conditions

In order to investigate whether OsDN-ITP7 transgenic rice can recapitulate the insect tolerance trait of AH30161 line, the OsDN-ITP7 transgenic rice was tested against ACB insect. The method is described in Example 8.
ACB Screening Results:
1) Results of First Validation Experiment After ACB neonate larvae inoculating seedlings for 5 days in the assays, the seedlings of ZH11-TC and DP0158 were significantly damaged by ACB insects, while the OsDN-ITP7 transgenic seedlings were less damaged, and the insects fed with the OsDN-ITP7 transgenic seedlings was smaller than that fed with ZH11-TC and DP0158 controls.

Ten OsDN-ITP7 transgenic lines were placed on one plate, and repeated for five times. Five days after ACB neonate larvae inoculation, 325 larvae in OsDN-ITP7 transgenic rice seedlings' well were found, 57 larvae developed to 1$^{st}$ instar, and 120 larvae developed to 2$^{nd}$ instar. 48 larvae in ZH11-TC seedlings' wells developed to 2$^{nd}$ instar. Similar results were obtained with DP0158 seedlings, 48 larvae

TABLE 17

Armyworm assay of OsDN-ITP6 transgenic rice under laboratory screening condition at line level (2$^{nd}$ experiment)

| Line ID | Number of larva at 1$^{st}$ instar | Number of larva at 2$^{nd}$ instar | Number of total observed larvae | Larvae growth inhibitory rate (%) | CK = ZH11-TC P value | CK = ZH11-TC P ≤ 0.05 | CK = DP0158 P value | CK = DP0158 P ≤ 0.05 |
|---|---|---|---|---|---|---|---|---|
| DP1759 (Construct) | 20 | 276 | 502 | 60.54 | 0.0060 | Y | 0.0004 | Y |
| ZH11-TC | 1 | 72 | 154 | 47.74 | | | | |
| DP0158 | 3 | 56 | 145 | 41.89 | | | | |
| DP1759.03 | 1 | 25 | 48 | 55.10 | 0.4194 | | 0.1783 | |
| DP1759.07 | 3 | 40 | 67 | 65.71 | 0.0098 | Y | 0.0018 | Y |
| DP1759.08 | 2 | 40 | 65 | 65.67 | 0.0118 | Y | 0.0023 | Y |
| DP1759.09 | 5 | 32 | 65 | 60.00 | 0.0673 | | 0.0161 | Y |
| DP1759.10 | 5 | 35 | 66 | 63.38 | 0.0266 | Y | 0.0055 | Y |
| DP1759.12 | 1 | 42 | 69 | 62.86 | 0.0284 | Y | 0.0060 | Y |
| DP1759.14 | 2 | 39 | 66 | 63.24 | 0.0303 | Y | 0.0066 | Y |
| DP1759.15 | 1 | 23 | 56 | 43.86 | 0.5488 | | 0.9908 | | developed to $2^{nd}$ instar. The average larva growth inhibitory rates of OsDN-ITP7 transgenic rice, ZH11-TC and DP0158 were 61%, 50% and 47%, respectively. The average larva growth inhibitory rate of OsDN-ITP7 transgenic rice was significantly greater than that of ZH11-TC and DP0158 control. These results show that over-expression of OsDN-ITP7 in rice significantly increased ACB insect tolerance of transgenic rice at construct level.

Further analysis at transgenic line level is displayed in Table 18. All the transgenic lines exhibited greater larva growth inhibitory rates than both ZH11-TC and DP0158 controls. Three lines exhibited significantly greater larva growth inhibitory rates than both ZH11-TC and DP0158 seedlings. These results further indicate OsDN-ITP7 plays a role in increasing ACB insect tolerance in rice compared to controls at line level.

of all the observed 182 larvae in ZH11-TC seedling's wells developed to $1^{st}$ instar, and 43 larvae developed to $2^{nd}$ instar; and eight larvae of the 162 larvae in DP0158 seedlings' wells developed to $1^{st}$ instar and 45 larvae developed to $2^{nd}$ instar. The average larva growth inhibitory rates of OsDN-ITP7 transgenic rice, ZH11-TC and DP0158 were 47%, 28% and 36%, respectively. The average larva growth inhibitory rate of OsDN-ITP7 transgenic rice was significantly greater than that of ZH11-TC and DP0158 control. These results show that over-expression of OsDN-ITP7 in rice increased ACB insect tolerance of transgenic rice at construct level.

Further analysis at transgenic line level is displayed in Table 19. Eight transgenic lines exhibited significantly greater larva growth inhibitory rates than ZH11-TC seedlings, and three lines exhibited significantly greater larva

TABLE 18

Asian corn borer assay of OsDN-ITP7 transgenic rice under laboratory screening condition at line level ($1^{st}$ experiment)

| Line ID | Number of larva at $1^{st}$ instar | Number of larva at $2^{nd}$ instar | Number of total observed larvae | Larvae growth inhibitory rate (%) | CK = ZH11-TC | | CK = DP0158 | |
|---|---|---|---|---|---|---|---|---|
| | | | | | P value | P ≤ 0.05 | P value | P ≤ 0.05 |
| DP1791 (Construct) | 57 | 120 | 325 | 61.26 | 0.0096 | | 0.0054 | |
| ZH11-TC | 15 | 48 | 142 | 49.68 | | | | |
| DP0158 | 12 | 48 | 142 | 46.75 | | | | |
| DP1791.01 | 7 | 16 | 34 | 73.17 | 0.0022 | Y | 0.0060 | Y |
| DP1791.03 | 4 | 12 | 34 | 52.63 | 0.7446 | | 0.5456 | |
| DP1791.04 | 4 | 13 | 33 | 56.76 | 0.4498 | | 0.3048 | |
| DP1791.06 | 9 | 6 | 24 | 72.73 | 0.0269 | Y | 0.0049 | Y |
| DP1791.07 | 5 | 10 | 30 | 57.14 | 0.3927 | | 0.2634 | |
| DP1791.08 | 4 | 13 | 33 | 56.76 | 0.4403 | | 0.2980 | |
| DP1791.09 | 10 | 10 | 33 | 69.77 | 0.0205 | Y | 0.0000 | Y |
| DP1791.10 | 1 | 16 | 32 | 54.55 | 0.6202 | | 0.4488 | |
| DP1791.12 | 4 | 13 | 32 | 58.33 | 0.3482 | | 0.2289 | |
| DP1791.13 | 9 | 11 | 40 | 59.18 | 0.2570 | | 0.0525 | |

2) Results of Second Validation Experiment

The same ten OsDN-ITP7 transgenic lines were tested in this second experiment with six repeats. Five days after inoculation, 556 larvae were found, 38 larvae developed to $1^{st}$ instar, and 205 larvae developed to $2^{nd}$ instar. Five larvae growth inhibitory rates than DP0158 seedlings. The result was same to that in the first validation experiment. These results further indicate OsDN-ITP7 plays a role in increasing ACB insect tolerance in rice compared to controls at line level.

TABLE 19

Asian corn borer assay of OsDN-ITP7 transgenic rice under laboratory screening condition at line level ($2^{nd}$ experiment)

| Line ID | Number of larva at $1^{st}$ instar | Number of larva at $2^{nd}$ instar | Number of total observed larvae | Larvae growth inhibitory rate (%) | CK = ZH11-TC | | CK = DP0158 | |
|---|---|---|---|---|---|---|---|---|
| | | | | | P value | P ≤ 0.05 | P value | P ≤ 0.05 |
| DP1791 (Construct) | 38 | 205 | 556 | 47.31 | 0.0000 | Y | 0.0124 | Y |
| ZH11-TC | 5 | 43 | 182 | 28.34 | | | | |
| DP0158 | 8 | 45 | 162 | 35.88 | | | | |
| DP1791.01 | 3 | 13 | 51 | 35.19 | 0.3372 | | 0.9263 | |
| DP1791.03 | 1 | 23 | 57 | 43.10 | 0.0399 | Y | 0.3309 | |
| DP1791.04 | 2 | 14 | 53 | 32.73 | 0.5324 | | 0.6724 | |
| DP1791.06 | 7 | 16 | 56 | 47.62 | 0.0069 | Y | 0.1084 | |
| DP1791.07 | 3 | 25 | 58 | 50.82 | 0.0022 | Y | 0.0456 | Y |
| DP1791.08 | 4 | 18 | 53 | 45.61 | 0.0184 | Y | 0.1963 | |
| DP1791.09 | 4 | 27 | 57 | 57.38 | 0.0001 | Y | 0.0051 | Y |
| DP1791.10 | 4 | 26 | 66 | 48.57 | 0.0035 | Y | 0.0730 | |
| DP1791.12 | 4 | 24 | 49 | 60.38 | 0.0000 | Y | 0.0027 | Y |
| DP1791.13 | 6 | 19 | 56 | 50.00 | 0.0029 | Y | 0.0568 | |

Example 13

OAW Assay of OsDN-ITP7 Transgenic Rice Plants Under Laboratory Conditions

OAW assay of OsDN-ITP7 transgenic rice was performed as described in Example 3. The screening results as below.

OAW Screening Results:

Ten OsDN-ITP7 transgenic rice lines were tested in OAW assay. These ten lines were placed on one 32-well plate with five repeats. Five days after co-culture, 517 larvae were found in the OsDN-ITP7 transgenic rice wells, wherein 30 larvae developed to $1^{st}$ instar and 161 OAW larvae developed to $2^{nd}$ instar, while five of the 112 larvae in the ZH11-TC wells developed to $1^{st}$ instar, 24 larvae developed to $2^{nd}$ instar; and one of 121 larvae in the DP0158 wells developed to $1^{st}$ instar and 28 developed to $2^{nd}$ instar. The average OAW larvae growth inhibitory rates of OsDN-ITP7 transgenic rice, ZH11-TC and DP0158 were 40%, 29% and 25%. The OAW larvae growth inhibitory rate of OsDN-ITP7 transgenic rice was significantly greater than ZH11-TC and DP0158 controls.

Analysis at line level was shown in Table 20. Nine lines had greater larvae growth inhibitory rates than both ZH11-TC and DP0158 controls. Three lines had significantly greater larvae growth inhibitory rates than ZH11-TC and DP0158 controls. These results demonstrate that OsDN-ITP7 transgenic rice had improved OAW tolerance at seedling stage.

TABLE 20

Armyworm assay of OsDN-ITP7 transgenic rice under laboratory screening condition at line level ($1^{st}$ experiment)

| Line ID | Number of larva at $1^{st}$ instar | Number of larva at $2^{nd}$ instar | Number of total observed larvae | Larvae growth inhibitory rate (%) | CK = ZH11-TC P value | CK = ZH11-TC P ≤ 0.05 | CK = DP0158 P value | CK = DP0158 P ≤ 0.05 |
|---|---|---|---|---|---|---|---|---|
| DP1791 (Construct) | 30 | 161 | 517 | 40.40 | 0.0257 | Y | 0.0025 | Y |
| ZH11-TC | 5 | 24 | 112 | 29.06 | | | | |
| DP0158 | 1 | 28 | 121 | 24.59 | | | | |
| DP1791.01 | 3 | 19 | 51 | 46.30 | 0.0246 | Y | 0.0053 | Y |
| DP1791.03 | 4 | 12 | 55 | 33.90 | 0.4972 | | 0.2034 | |
| DP1791.04 | 0 | 18 | 49 | 36.73 | 0.3193 | | 0.1203 | |
| DP1791.06 | 7 | 12 | 54 | 42.62 | 0.0709 | Y | 0.0172 | Y |
| DP1791.07 | 3 | 26 | 52 | 58.18 | 0.0006 | Y | 0.0001 | Y |
| DP1791.08 | 1 | 11 | 52 | 24.53 | 0.5948 | | 0.9815 | |
| DP1791.09 | 2 | 16 | 50 | 38.46 | 0.2136 | | 0.0705 | Y |
| DP1791.10 | 5 | 18 | 47 | 53.85 | 0.0028 | Y | 0.0005 | Y |
| DP1791.12 | 1 | 15 | 54 | 30.91 | 0.7886 | | 0.3961 | |
| DP1791.13 | 4 | 14 | 53 | 38.60 | 0.1868 | | 0.0576 | |

In the second experiment, five days later after inoculation of OAW neonate larvae, 573 larvae were found in the OsDN-ITP7 transgenic rice well, 14 larvae grew to $1^{st}$ instar and 249 larvae grew to $2^{nd}$ instar. The larvae growth inhibitory rate was 47%. Whereas, two larvae of 148 in the ZH11-TC seedling wells grew to $1^{st}$ instar, and 53 larvae grew to $2^{nd}$ instar, and two larvae of the 136 larvae in DP0158 seedling wells grew to $1^{st}$ instar and 56 larvae grew to $2^{nd}$ instar. The OAW larvae growth inhibitory rate of OsDN-ITP7 transgenic rice was significantly greater than ZH11-TC control. These results indicate that OsDN-ITP7 transgenic rice exhibited OAW larvae tolerance at construct level.

Analysis at line level shows that seven lines had greater larvae growth inhibitory rates than both ZH11-TC and DP0158 controls (Table 21). These results further confirm that over-expression OsDN-ITP7 enhanced tolerance against OAW insect in transgenic rice plants, and OsDN-ITP7 plays a role in increasing OAW insect tolerance.

TABLE 21

Armyworm assay of OsDN-ITP7 transgenic rice under laboratory screening condition at line level (2$^{nd}$ experiment)

| Line ID | Number of larva at 1$^{st}$ instar | Number of larva at 2$^{nd}$ instar | Number of total observed larvae | Larvae growth inhibitory rate (%) | CK = ZH11-TC P value | CK = ZH11-TC P ≤ 0.05 | CK = DP0158 P value | CK = DP0158 P ≤ 0.05 |
|---|---|---|---|---|---|---|---|---|
| DP1791 (Construct) | 14 | 249 | 573 | 47.19 | 0.0477 | Y | 0.4081 | |
| ZH11-TC | 2 | 53 | 148 | 38.00 | | | | |
| DP0158 | 2 | 56 | 136 | 43.48 | | | | |
| DP1791.01 | 0 | 23 | 69 | 33.33 | 0.4784 | | 0.1590 | |
| DP1791.03 | 1 | 19 | 55 | 37.50 | 0.9843 | | 0.4890 | |
| DP1791.04 | 5 | 21 | 61 | 46.97 | 0.2375 | | 0.6526 | |
| DP1791.06 | 0 | 19 | 46 | 41.30 | 0.6498 | | 0.8564 | |
| DP1791.07 | 4 | 26 | 52 | 60.71 | 0.0045 | Y | 0.0287 | Y |
| DP1791.08 | 0 | 28 | 63 | 44.44 | 0.3904 | | 0.8886 | |
| DP1791.09 | 1 | 31 | 60 | 54.10 | 0.0342 | Y | 0.1563 | |
| DP1791.10 | 1 | 27 | 56 | 50.88 | 0.1101 | | 0.3650 | |
| DP1791.12 | 0 | 25 | 52 | 48.08 | 0.1955 | | 0.5335 | |
| DP1791.13 | 2 | 30 | 59 | 55.74 | 0.0253 | Y | 0.1230 | |

What is claimed is:

1. A transgenic plant, plant cell or seed, comprising in its genome a recombinant DNA construct comprising a polynucleotide encoding a polypeptide comprising an amino acid sequence having at least 95% identity to SEQ ID NO: 6 operably linked to at least one heterologous regulatory element, wherein the plant, plant cell or seed has an increased tolerance to a Lepidopteran insect pest as compared to a control plant not comprising the recombinant DNA construct.

2. The transgenic plant or plant cell of claim 1, wherein the polynucleotide comprises SEQ ID NO: 4 or SEQ ID NO: 5.

3. The transgenic plant or plant cell of claim 1, wherein the polynucleotide encodes a polypeptide comprising the amino acid sequence of SEQ ID NO: 6.

4. The transgenic plant or plant cell of claim 1, wherein the Lepidopteran insect pest is Asian Corn Borer (*Ostrinia furnacalis*), Rice Stem Borer (*Chilo suppressalis*), or Oriental Armyworm (*Mythimna separata*).

5. The transgenic plant of claim 1, wherein the plant is selected from the group consisting of rice, maize, soybean, sunflower, sorghum, canola, wheat, alfalfa, cotton, barley, millet, sugar cane and switchgrass.

6. A method of increasing tolerance in a plant to a Lepidopteran insect pest, comprising
  (a) introducing into a regenerable plant cell a recombinant DNA construct comprising a polynucleotide operably linked to at least one regulatory element, wherein the polynucleotide encodes a polypeptide having an amino acid sequence of at least 95% identity compared to SEQ ID NO: 6;
  (b) regenerating a transgenic plant from the regenerable plant cell after step (a), wherein the transgenic plant comprises in its genome the recombinant DNA construct; and
  (c) obtaining a progeny plant derived from the transgenic plant of step (b), wherein the progeny plant comprises in its genome the recombinant DNA construct and exhibits increased tolerance to a Lepidopteran insect pest when compared to a control plant not comprising the recombinant DNA construct.

7. The method of claim 6, wherein the Lepidopteran insect pest is Asian Corn Borer (*Ostrinia furnacalis*), Rice Stem Borer (*Chilo suppressalis*), or Oriental Armyworm (*Mythimna separata*).

8. A method of evaluating tolerance in a plant to a Lepidopteran insect pest, comprising:
  (a) introducing into a regenerable plant cell a recombinant DNA construct comprising a polynucleotide operably linked to at least one regulatory element, wherein the polynucleotide encodes a polypeptide having an amino acid sequence of at least 95% identity when compared to SEQ ID NO: 6;
  (b) regenerating a transgenic plant from the regenerable plant cell after step (a), wherein the transgenic plant comprises in its genome the recombinant DNA construct;
  (c) obtaining a progeny plant derived from the transgenic plant, wherein the progeny plant comprises in its genome the recombinant DNA construct; and
  (d) evaluating the progeny plant for tolerance to a Lepidopteran insect pest compared to a control plant not comprising the recombinant DNA construct.

9. The method of claim 8, wherein the Lepidopteran insect pest is Asian Corn Borer (*Ostrinia furnacalis*), Rice Stem Borer (*Chilo suppressalis*), or Oriental Armyworm (*Mythimna separata*).

* * * * *

SEQUENCE LISTING

<160> NUMBER OF SEQ ID NOS: 24

<210> SEQ ID NO 1
<211> LENGTH: 496
<212> TYPE: DNA
<213> ORGANISM: Oryza sativa

<400> SEQUENCE: 1

```
ttctctggcg tggtcggctg gttcagctag ccggtcagat gcatggagcg gatagagtcg      60
atttctcttg tacgagtaga tcacggaagg aatgatgata ttttcgtac ataggcctag     120
agaatttta gggcgtttcg tagtggatgg gtcaatgtat ggagcactgt gttttaataa     180
gacgggaaag ctggaatcca agtagaaact cctggagaca ccgccgcgcc ggggggacaa     240
gcatcgtgat cggtaggaag gcgatgagcg ggagaacaac gatacttgct taggtcgagt     300
acgttagatc ttccgcgttc ttttcggcaa ttcggcccac tgaacacggc tggtcttgcg     360
gcccacagta gcggttggca atgtcagttt attgacttcc tgagctcaag ctacgcctct     420
ctgaccatgg aatcgttttt ttttttcttt ctcgaaacaa aaatacaaac ataaagctcg     480
tgtacatact tcccat                                                      496
```

<210> SEQ ID NO 2
<211> LENGTH: 517
<212> TYPE: DNA
<213> ORGANISM: Oryza sativa

<400> SEQUENCE: 2

```
ctaatagaaa tataagtgca aaacagagaa ttgcaaaata taggaaaaat acaaaaatga      60
tcatttgatt ggactccagg aaatacatag gaatcggacg agcaagatag actcaaaggg     120
atatttccaa gaggttgtag ctcttactaa atttcctcca aaatctttat aggattgttc     180
attccatagg aatttcaaaa gataacatat aattcaatct tttgtttcaa aggttttcat     240
atgaaatttt actataggat tgaaattatc caaaatttat atgatcttcc tccaaatcaa     300
aggggcccct ataaaagtga ggtcttttt taagatgca gattgtactt tattttcgtt     360
agtatgtttt cctaatctga aaaacgatat gttttgtgtg aaaaccttat ataaaaagtt     420
```

```
gctctaaaat atcaaataaa tctattttta aatttataat aattaaaact taattaatca      480
tgcgttaata ttttttttat tttacgtgcc cttgctt                              517

<210> SEQ ID NO 3
<211> LENGTH: 753
<212> TYPE: DNA
<213> ORGANISM: Oryza sativa

<400> SEQUENCE: 3
ctttatgtcg aagatctcat tcaccttttt gtacacatga agattggtga caacttttt       60 gccttcaata attacattga aacttcgatt tggtattggg tggaaatctg catcatcttg     120
atttgattta gttgtaattg cctattttta tcttagaaat atcaatagta tatcggtttg     180
ttattggcaa tgtcattttg gaattggcta ttactacatt ttatctcatt tagttatgtg     240
ctgttgagta attaccctat gaattttata cagatacatt gccgtgggaa atgagccgtt     300
cttgacgagc taccagggtc aattccagtc atatgttatt ccagcaatga caaacattca     360
gcaatcgctg gtgaaggcta atcttgctag ctatgtgaag cttgttgtcc catgcaatgc     420
tgatgcttat cagagtgctt ctctcccatc acaaggagtt tttaggactg aactgactca     480
gataatgacc cagctcgccg cttttctcag ttctagtgga gcgccatttg tggtcaatat     540 atacccttt ctcagtcttt atcagagctc tgactttcca caagattatg ccttcttcga     600
gggatctact cacccggttg tagatggtcc taacacatac tacaatgctt ttgatgcaa      660 ctttgacaca ttagttgctg cgctgggtaa aattggatat ggacagctac cgattgcaat     720
tggtgaagtt ggctggccaa ctgaaggagc acc                                  753

<210> SEQ ID NO 4
<211> LENGTH: 1806
<212> TYPE: DNA
<213> ORGANISM: Oryza sativa

<400> SEQUENCE: 4
gtggagagat ttggaggaga ggagcgcgcg gtgaggaggc ggtggaggcg gaagcggcga      60
cgagttggcg agaagcgcag cagcgacgga cgacgagcaa ccggcgggcg acgagggcag    120
gaagagggct gctcctcccc ctccgcctcc gccgccggcc gacgccgtca tgggggagtc    180
gctgctcacc gcgctctcca tggacaccac cacgggccac cacccgcacc agggcccctc    240
cacgttcctc tccatggaca ccgcctccca cgacgacttc gacctcttcc tcccgccgcc    300
gccggggccg ttccgccgct gcctccatgc cgcggccgcc gcccccctg acatcaacct     360 ccccctcgac gccgaccct cccctccgcc tccggctctg cagtccggcg ccctccacga    420
ccccaacgtc gacatgcttg atgtcggcct cggcggcccg cagctttacg actcggactc    480
acctgctgcc accaccggcg tgtccctgc cccggccgcc gcgaccacca cggtcgccgt    540
atcacatgcc aagggctcca attccagcgc tgcccgcaag tgcgtgaaga ggaacgatac    600
catatggggc gcgtggttct tcttcaccca ctacttcaag ccggtcatgt cggctgacaa    660
gaacggcaag gcgaaggccc ccaccgccgg tgggaacggt aataatgcta cgctggatgc    720
tttcctagtg cagcacgaca tggagaacat gtacatgtgg gtgttcaagg agcggccaga    780
gaatgccctg gggaagatgc agctaaggag cttcatgaac gggcactcgc gccttgggga    840
gcctcagttc ccgttcagcg cggagaaagg gttcgtgcgc tcacaccgca tgcagcgcaa    900
gcactaccgg gggctgtcca acccgcagtg cctgcacggg atcgagatcg tccgggcacc    960
aaacttggct ggtgtgcccg aagctgattt gaagaggtgg acagagctca ccggaaggga   1020
```

-continued

```
cgctaacttc tcgattgatg ctgaggcgag tgattatgag tcatggagaa atcttcctag        1080
cacagatttt gagcttgaga ggccagcaac tactgctgcc acgaagacta gctcacatgg        1140
ccatcacaag aagttgctca acggttctgg ccttaacctg tcaacacagc catcgaatca        1200
cagctctggg gatggtctgg acatcccaaa tatttgcaac aagcgccgga aggattcctc        1260
ccccacagcg atggaagaag attgcagcaa ttcaaattca gacaaggtcc aggacatgga        1320
agtgagccac acgttcgagc cgtcatggat gaatgacttc actggtgtga tgcgccatgc        1380
ttctggtcca gtgactgcag caaaaacaat ctatgaagat agcaaggggt acttgatcat        1440
cattagccta ccgtttgctg atatacaaag ggtgaaggtt tcatggaaga atactcttac        1500
aaatgggata gttaaggtat catgcactag tgttggccgg atgccattct gaagagaca         1560 tgaccggacc ttcaagttag tcgatcctac acctgagcat tgtccaccag gagagtttat        1620
tcgggaaatt ccactcccta ctcggatccc ggaagatgct actttagaag catactgtga        1680
tgaatcagga acaggcctag agattattgt tccaaaatac cgtgttggtc ctgaagaaca        1740
tgaagttcat gtgtccatga ggcccccctc gtcatggtgc cagtcttaac atgttcaagg        1800
tgtgtg                                                                    1806
```

<210> SEQ ID NO 5
<211> LENGTH: 1620
<212> TYPE: DNA
<213> ORGANISM: Oryza sativa

<400> SEQUENCE: 5

```
atgggggagt cgctgctcac cgcgctctcc atggacacca ccacggccca ccacccgcac          60
cagggcccct ccacgttcct ctccatggac accgcctccc acgacgactt cgacctcttc         120
ctcccgccgc cgccggggcc gttccgccgc tgcctccatg ccgcggccgc cgccccccct         180
gacatcaacc tcccccctcga cgccgacccc tccctccgc ctccggctct gcagtccggc         240
gccctccacg accccaacgt cgacatgctt gatgtcggcc tcggcggccc gcagctttac         300
gactcggact cacctgctgc caccaccggc gtgtccctg ccccggccgc cgcgaccacc          360
acggtcgccg tatcacatgc caagggctcc aattccagcc ctgcccgcaa gtgcgtgaag         420
aggaacgata ccatatgggg cgcgtggttc ttcttcaccc actacttcaa gccggtcatg         480
tcggctgaca agaacggcaa ggcgaaggcc cccaccgccg tgggaacgg taataatgct          540 acgctggatg ctttcctagt gcagcacgac atggagaaca tgtacatgtg ggtgttcaag         600
gagcggccag agaatgccct ggggaagatg cagctaagga gcttcatgaa cgggcactcg         660
cgccttgggg agcctcagtt cccgttcagc gcggagaaag ggttcgtgcg ctcacaccgc         720
atgcagcgca agcactaccg ggggctgtcc aacccgcagt gcctgcacgg gatcgagatc         780
gtccgggcac caaacttggc tggtgtgccc gaagctgatt tgaagaggtg gacagagctc         840
accggaaggg acgctaactt ctcgattgat gctgaggcga gtgattatga gtcatggaga         900
aatcttccta gcacagattt tgagcttgag aggccagcaa ctactgctgc cacgaagact         960
agctcacatg gccatcacaa gaagttgctc aacggttctg gccttaacct gtcaacacag        1020
ccatcgaatc acagctctgg ggatggtctg gacatcccaa atatttgcaa caagcgccgg        1080
aaggattcct ccccacagc gatggaagaa gattgcagca attcaaattc agacaaggtc         1140
caggacatgg aagtgagcca cacgttcgag ccgtcatgga tgaatgactt cactggtgtg        1200
atgcgccatg cttctggtcc agtgactgca gcaaaaacaa tctatgaaga tagcaagggg        1260
```

```
tacttgatca tcattagcct accgtttgct gatatacaaa gggtgaaggt tcatggaag    1320 aatactctta caaatgggat agttaaggta tcatgcacta gtgttggccg gatgccattc   1380
ttgaagagac atgaccggac cttcaagtta gtcgatccta cacctgagca ttgtccacca   1440
ggagagttta ttcgggaaat tccactccct actcggatcc cggaagatgc tactttagaa   1500
gcatactgtg atgaatcagg aacaggccta gagattattg ttccaaaata ccgtgttggt   1560
cctgaagaac atgaagttca tgtgtccatg aggccccccct cgtcatggtg ccagtcttaa  1620
```

<210> SEQ ID NO 6
<211> LENGTH: 539
<212> TYPE: PRT
<213> ORGANISM: Oryza sativa

<400> SEQUENCE: 6

```
Met Gly Glu Ser Leu Leu Thr Ala Leu Ser Met Asp Thr Thr Thr Ala
1               5                   10                  15

His His Pro His Gln Gly Pro Ser Thr Phe Leu Ser Met Asp Thr Ala
            20                  25                  30

Ser His Asp Asp Phe Asp Leu Phe Leu Pro Pro Pro Gly Pro Phe
        35                  40                  45

Arg Arg Cys Leu His Ala Ala Ala Ala Ala Pro Pro Asp Ile Asn Leu
    50                  55                  60

Pro Leu Asp Ala Asp Pro Ser Pro Pro Pro Ala Leu Gln Ser Gly
65                  70                  75                  80

Ala Leu His Asp Pro Asn Val Asp Met Leu Asp Val Gly Leu Gly Gly
                85                  90                  95

Pro Gln Leu Tyr Asp Ser Asp Ser Pro Ala Ala Thr Thr Gly Val Ser
            100                 105                 110

Pro Ala Pro Ala Ala Ala Thr Thr Thr Val Ala Val Ser His Ala Lys
        115                 120                 125

Gly Ser Asn Ser Ser Ala Ala Arg Lys Cys Val Lys Arg Asn Asp Thr
    130                 135                 140

Ile Trp Gly Ala Trp Phe Phe Thr His Tyr Phe Lys Pro Val Met
145                 150                 155                 160

Ser Ala Asp Lys Asn Gly Lys Ala Lys Ala Pro Thr Ala Gly Gly Asn
                165                 170                 175

Gly Asn Asn Ala Thr Leu Asp Ala Phe Leu Val Gln His Asp Met Glu
            180                 185                 190

Asn Met Tyr Met Trp Val Phe Lys Glu Arg Pro Glu Asn Ala Leu Gly
        195                 200                 205

Lys Met Gln Leu Arg Ser Phe Met Asn Gly His Ser Arg Leu Gly Glu
    210                 215                 220

Pro Gln Phe Pro Phe Ser Ala Glu Lys Gly Phe Val Arg Ser His Arg
225                 230                 235                 240

Met Gln Arg Lys His Tyr Arg Gly Leu Ser Asn Pro Gln Cys Leu His
                245                 250                 255

Gly Ile Glu Ile Val Arg Ala Pro Asn Leu Ala Gly Val Pro Glu Ala
            260                 265                 270

Asp Leu Lys Arg Trp Thr Glu Leu Thr Gly Arg Asp Ala Asn Phe Ser
        275                 280                 285

Ile Asp Ala Glu Ala Ser Asp Tyr Glu Ser Trp Arg Asn Leu Pro Ser
    290                 295                 300

Thr Asp Phe Glu Leu Glu Arg Pro Ala Thr Thr Ala Ala Thr Lys Thr
305                 310                 315                 320
```

```
Ser Ser His Gly His His Lys Lys Leu Leu Asn Gly Ser Gly Leu Asn
            325                 330                 335
Leu Ser Thr Gln Pro Ser Asn His Ser Ser Gly Asp Gly Leu Asp Ile
            340                 345                 350
Pro Asn Ile Cys Asn Lys Arg Arg Lys Asp Ser Ser Pro Thr Ala Met
            355                 360                 365
Glu Glu Asp Cys Ser Asn Ser Asn Ser Asp Lys Val Gln Asp Met Glu
            370                 375                 380
Val Ser His Thr Phe Glu Pro Ser Trp Met Asn Asp Phe Thr Gly Val
385                 390                 395                 400
Met Arg His Ala Ser Gly Pro Val Thr Ala Ala Lys Thr Ile Tyr Glu
            405                 410                 415
Asp Ser Lys Gly Tyr Leu Ile Ile Ile Ser Leu Pro Phe Ala Asp Ile
            420                 425                 430
Gln Arg Val Lys Val Ser Trp Lys Asn Thr Leu Thr Asn Gly Ile Val
            435                 440                 445
Lys Val Ser Cys Thr Ser Val Gly Arg Met Pro Phe Leu Lys Arg His
            450                 455                 460
Asp Arg Thr Phe Lys Leu Val Asp Pro Thr Pro Glu His Cys Pro Pro
465                 470                 475                 480
Gly Glu Phe Ile Arg Glu Ile Pro Leu Pro Thr Arg Ile Pro Glu Asp
            485                 490                 495
Ala Thr Leu Glu Ala Tyr Cys Asp Glu Ser Gly Thr Gly Leu Glu Ile
            500                 505                 510
Ile Val Pro Lys Tyr Arg Val Gly Pro Glu Glu His Glu Val His Val
            515                 520                 525
Ser Met Arg Pro Pro Ser Ser Trp Cys Gln Ser
530                 535
```

<210> SEQ ID NO 7
<211> LENGTH: 600
<212> TYPE: DNA
<213> ORGANISM: Oryza sativa

<400> SEQUENCE: 7

```
atacacaaag cgtacctgtt ctttcggtgt ctttgttcca gaagccagaa aaactgcgag    60
catgggcaaa ttcggtggag ctgcggtcct tccagtatac cgtgaagaag aagatgaaga   120
cttgttcgag acatcatcgt ccatctcagg cgactccgat gatgaggctc aattttcaga   180
cagcgaggaa gctgaagctc aagaagacca gtttgcgcag cagccagcga aaggatgaa    240
ttcagatagc ctctacgatc tgtcatctat gaaggcacaa ctccctgtca agaaaggatt   300
atccaaatac tacgacggaa agtctcaatc ttttgcatgt atgtctgagg tgagatgcct   360
agaggatcta cgcaagaagg agaatccata caagaagatc aaatcatcca agagctatgt   420
agcactggat gggaaccagg aagcttgtca tatacctggc gcaaacagca catcaatagc   480
caagaagtct ggaagttctt gcgcaaatct gatggccagg aataacacca aaagcatgct   540
ctataggcct cccccaattc ctgtaaacaa aagcggatat catcagtagg aacagtatcg   600
```

<210> SEQ ID NO 8
<211> LENGTH: 528
<212> TYPE: DNA
<213> ORGANISM: Oryza sativa

<400> SEQUENCE: 8

```
atgggcaaat cggtggagc tgcggtcctt ccagtatacc gtgaagaaga agatgaagac    60
ttgttcgaga catcatcgtc catctcaggc gactccgatg atgaggctca attttcagac   120
agcgaggaag ctgaagctca agaagaccag tttgcgcagc agccagcgag aaggatgaat   180
tcagatagcc tctacgatct gtcatctatg aaggcacaac tccctgtcaa gaaaggatta   240
tccaaatact acgacggaaa gtctcaatct tttgcatgta tgtctgaggt gagatgccta   300
gaggatctac gcaagaagga gaatccatac aagaagatca atcatccaa gagctatgta   360 gcactggatg ggaaccagga agcttgtcat atacctggcg caaacagcac atcaatagcc   420
aagaagtctg gaagttcttg cgcaaatctg atggccagga ataacaccaa agcatgctc    480 tataggcctc ccccaattcc tgtaaacaaa agcggatatc atcagtag                528
```

<210> SEQ ID NO 9
<211> LENGTH: 175
<212> TYPE: PRT
<213> ORGANISM: Oryza sativa

<400> SEQUENCE: 9

```
Met Gly Lys Phe Gly Gly Ala Ala Val Leu Pro Val Tyr Arg Glu Glu
1               5                   10                  15

Glu Asp Glu Asp Leu Phe Glu Thr Ser Ser Ile Ser Gly Asp Ser
            20                  25                  30

Asp Asp Glu Ala Gln Phe Ser Asp Ser Glu Glu Ala Glu Ala Gln Glu
        35                  40                  45

Asp Gln Phe Ala Gln Gln Pro Ala Arg Arg Met Asn Ser Asp Ser Leu
    50                  55                  60

Tyr Asp Leu Ser Ser Met Lys Ala Gln Leu Pro Val Lys Lys Gly Leu
65                  70                  75                  80

Ser Lys Tyr Tyr Asp Gly Lys Ser Gln Ser Phe Ala Cys Met Ser Glu
                85                  90                  95

Val Arg Cys Leu Glu Asp Leu Arg Lys Lys Glu Asn Pro Tyr Lys Lys
            100                 105                 110

Ile Lys Ser Ser Lys Ser Tyr Val Ala Leu Asp Gly Asn Gln Glu Ala
        115                 120                 125

Cys His Ile Pro Gly Ala Asn Ser Thr Ser Ile Ala Lys Lys Ser Gly
    130                 135                 140

Ser Ser Cys Ala Asn Leu Met Ala Arg Asn Asn Thr Lys Ser Met Leu
145                 150                 155                 160

Tyr Arg Pro Pro Ile Pro Val Asn Lys Ser Gly Tyr His Gln
                165                 170                 175
```

<210> SEQ ID NO 10
<211> LENGTH: 244
<212> TYPE: DNA
<213> ORGANISM: Oryza sativa

<400> SEQUENCE: 10

```
tggaagtgga gcaaggttga gttacctgtg agacagtaat gaagaggaac accatccttg    60
ctctcttcat ctgggccatg gctatggtga tcttcgccac ggcaatgccg gccaaggcaa   120
ggatggaggg gatccatcct caaggatgca gatgctgcta tttcagactt aggccgatga   180
tccagtgtgc caaggcttgc tgtggctctg acgatgagaa ctgctgcctt gtgaacaact   240
agtt                                                                244
```

<210> SEQ ID NO 11

```
<211> LENGTH: 204
<212> TYPE: DNA
<213> ORGANISM: Oryza sativa

<400> SEQUENCE: 11
atgaagagga acaccatcct tgctctcttc atctgggcca tggctatggt gatcttcgcc    60
acggcaatgc cggccaaggc aaggatggag gggatccatc ctcaaggatg cagatgctgc   120
tatttcagac ttaggccgat gatccagtgt gccaaggctt gctgtggctc tgacgatgag   180
aactgctgcc ttgtgaacaa ctag                                          204

<210> SEQ ID NO 12
<211> LENGTH: 67
<212> TYPE: PRT
<213> ORGANISM: Oryza sativa

<400> SEQUENCE: 12

Met Lys Arg Asn Thr Ile Leu Ala Leu Phe Ile Trp Ala Met Ala Met
 1               5                  10                  15

Val Ile Phe Ala Thr Ala Met Pro Ala Lys Ala Arg Met Glu Gly Ile
                20                  25                  30

His Pro Gln Gly Cys Arg Cys Cys Tyr Phe Arg Leu Arg Pro Met Ile
            35                  40                  45

Gln Cys Ala Lys Ala Cys Cys Gly Ser Asp Asp Glu Asn Cys Cys Leu
        50                  55                  60

Val Asn Asn
65

<210> SEQ ID NO 13
<211> LENGTH: 33
<212> TYPE: DNA
<213> ORGANISM: Artificial Sequence
<220> FEATURE:
<223> OTHER INFORMATION: Forward primer for cloning cDNA of OsSLT1 gene

<400> SEQUENCE: 13
ctgctgaggg tggagagatt tggaggagag gag                                 33

<210> SEQ ID NO 14
<211> LENGTH: 35
<212> TYPE: DNA
<213> ORGANISM: Artificial Sequence
<220> FEATURE:
<223> OTHER INFORMATION: Reverse primer for cloning cDNA of OsSLT1 gene

<400> SEQUENCE: 14
ccgctgaggc acacaccttg aacatgttaa gactg                               35

<210> SEQ ID NO 15
<211> LENGTH: 26
<212> TYPE: DNA
<213> ORGANISM: Artificial Sequence
<220> FEATURE:
<223> OTHER INFORMATION: Forward primer for cloning cDNA of OsDN-ITP6
      gene

<400> SEQUENCE: 15
atacacaaag cgtacctgtt ctttcg                                         26

<210> SEQ ID NO 16
<211> LENGTH: 27
<212> TYPE: DNA
<213> ORGANISM: Artificial Sequence
```

```
<220> FEATURE:
<223> OTHER INFORMATION: Reverse primer for cloning cDNA of OsDN-ITP6
      gene

<400> SEQUENCE: 16
cgatactgtt cctactgatg atatccg                                        27

<210> SEQ ID NO 17
<211> LENGTH: 34
<212> TYPE: DNA
<213> ORGANISM: Artificial Sequence
<220> FEATURE:
<223> OTHER INFORMATION: Forward primer for cloning cDNA of OsDN-ITP7
      gene

<400> SEQUENCE: 17
ctgctgaggt ggaagtggag caaggttgag ttac                                34

<210> SEQ ID NO 18
<211> LENGTH: 33
<212> TYPE: DNA
<213> ORGANISM: Artificial Sequence
<220> FEATURE:
<223> OTHER INFORMATION: Reverse primer for cloning cDNA of OsDN-ITP7
      gene

<400> SEQUENCE: 18
ccgctgagga actagttgtt cacaaggcag cag                                 33

<210> SEQ ID NO 19
<211> LENGTH: 22
<212> TYPE: DNA
<213> ORGANISM: Artificial Sequence
<220> FEATURE:
<223> OTHER INFORMATION: Forward primer for real-time PCR analysis of
      OsSLT1 gene

<400> SEQUENCE: 19
cggaccttca agttagtcga tc                                             22

<210> SEQ ID NO 20
<211> LENGTH: 21
<212> TYPE: DNA
<213> ORGANISM: Artificial Sequence
<220> FEATURE:
<223> OTHER INFORMATION: Reverse primer for real-time PCR analysis of
      OsSLT1 gene

<400> SEQUENCE: 20
ccgagtaggg agtggaattt c                                              21

<210> SEQ ID NO 21
<211> LENGTH: 22
<212> TYPE: DNA
<213> ORGANISM: Artificial Sequence
<220> FEATURE:
<223> OTHER INFORMATION: Forward primer for real-time PCR analysis of
      OsDN-ITP6 gene

<400> SEQUENCE: 21
ctatgtagca ctggatggga ac                                             22

<210> SEQ ID NO 22
<211> LENGTH: 21
<212> TYPE: DNA
<213> ORGANISM: Artificial Sequence
<220> FEATURE:
```

```
<223> OTHER INFORMATION: Reverse primer for real-time PCR analysis of
      OsDN-ITP6 gene

<400> SEQUENCE: 22
gcttttggtg ttattcctgg c                                              21

<210> SEQ ID NO 23
<211> LENGTH: 21
<212> TYPE: DNA
<213> ORGANISM: Artificial Sequence
<220> FEATURE:
<223> OTHER INFORMATION: Forward primer for real-time PCR analysis of
      OsDN-ITP7 gene

<400> SEQUENCE: 23
tgctatttca gacttaggcc g                                              21

<210> SEQ ID NO 24
<211> LENGTH: 19
<212> TYPE: DNA
<213> ORGANISM: Artificial Sequence
<220> FEATURE:
<223> OTHER INFORMATION: Reverse primer for real-time PCR analysis of
      OsDN-ITP7 gene

<400> SEQUENCE: 24
aaggcagcag ttctcatcg                                                 19
```